(12) United States Patent
Rao et al.

(10) Patent No.: US 7,211,431 B2
(45) Date of Patent: May 1, 2007

(54) EXPRESSION CASSETTES FOR PRODUCING PLANTS WITH INCREASED LEVELS OF ESSENTIAL AMINO ACIDS

(75) Inventors: Aragula Gururaj Rao, Urbandale, IA (US); Keith R. Roesler, Urbandale, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 240 days.

(21) Appl. No.: 10/919,048

(22) Filed: Aug. 16, 2004

(65) Prior Publication Data

US 2005/0010973 A1    Jan. 13, 2005

Related U.S. Application Data

(63) Continuation of application No. 09/311,689, filed on May 13, 1999, now Pat. No. 6,800,726, which is a continuation-in-part of application No. 08/740,682, filed on Nov. 1, 1996, now abandoned, and a continuation-in-part of application No. 09/297,418, filed on Apr. 30, 1999, now abandoned.

(51) Int. Cl.
     *C12N 15/00*      (2006.01)
     *C07H 21/04*      (2006.01)

(52) U.S. Cl. .................................. 435/320; 536/23.6

(58) Field of Classification Search .................. None
See application file for complete search history.

(56) References Cited

U.S. PATENT DOCUMENTS

| | | | |
|---|---|---|---|
| 5,258,300 A | 11/1993 | Glassman et al. | |
| 5,527,487 A | 6/1996 | Mikkelsen et al. | |
| 5,597,945 A | 1/1997 | Jaynes et al. | |
| 5,674,833 A | 10/1997 | Mikkelsen et al. | |
| 5,811,654 A | 9/1998 | Jaynes et al. | |
| 6,160,208 A | 12/2000 | Lundquist et al. | |
| 6,169,232 B1 | 1/2001 | Hey et al. | |

FOREIGN PATENT DOCUMENTS

| | | |
|---|---|---|
| EP | 0 467 839 A1 | 1/1992 |
| EP | 0 485 970 A2 | 5/1992 |
| EP | 0 485 970 A3 | 5/1992 |
| WO | WO 90/07862 A2 | 7/1990 |
| WO | WO 92/05239 * | 4/1992 |
| WO | WO 92/05239 A1 | 4/1992 |
| WO | WO 93/20175 A1 | 10/1993 |
| WO | WO 94/10315 A2 | 5/1994 |
| WO | WO 94/16078 A2 | 7/1994 |

(Continued)

OTHER PUBLICATIONS

Waye et al. (1995) Miami Winter BioTechnol. Symp. Proc., vol. 6, pp. 90.*

(Continued)

*Primary Examiner*—David J. Steadman
*Assistant Examiner*—Alexander Kim
(74) *Attorney, Agent, or Firm*—Pioneer Hi-Bred International, Inc.; Kathryn K. Lappegard

(57) ABSTRACT

The invention provides expression cassettes comprising isolated nucleic acids from modified *Hordeum vulgare* CI-2 polypeptides that are involved in enhancing the essential amino acid content of a plant.

1 Claim, 2 Drawing Sheets

```
                                      SEQUENCES OF BHL PROTEINS
                  10        20        30        40        50        60        70        80
                   *         *         *         *         *         *         *         *
WT CI - 2 (native)  SSVEKKPEGVNTGAGDRHNLKTEWPELVGKSVEEAKKVILQDKPEAQIIVLPVGTIVTMEYRIDRVRLFVDKLDNIAQVPRVG
WT CI-2                                     MNLKTEWPELVGKSVEEAKKVILQDKPEAQIIVLPVGTIVTMEYRIDRVRLFVDKLDNIAQVPRVG
BHL1                                        MKLKTEWPELVGKSVEKAKKVILKDKPEAQIIVLPVGTKVTKEYKIDRVKLFVDKKDNIAQVPRVG
BHL2                                        MKLKTEWPELVGKSVEKAKKVILKDKPEAQIIVLPVGTKVAKAYKIDKVKLFVDKKDNIAQVPRVG
BHL3                                        MKLKTEWPELVGKSVEKAKKVILKDKPEAQIIVLPVGTKVGKHYKIDKVKLFVDKKDNIAQVPRVG
BHL3N                   MKSVEKKPKGVKTGAGDKHKLKTEWPELVGKSVEKAKKVILKDKPEAQIIVLPVGTKVGKHYKIDKVKLFVDKKDNIAQVPRVG
BHL4                                        MKLKTEWPELVGKSVEKAKKVILKDKPEAQIIVLPVGTKVTGEYKIDRVKLFVDKKDNIAQVPRVG
BHL5                                        MAKMKTTWPELVGKTVEKAKKMIMKDKPEAKIMVLPVGTKVTGEWKMDRVKLWVDKKDKIAKTPKVG
BHL6                                        MAKMKTTWPELVGKTVEKAKKMIMKDKPEAKIMVLPVGTKVTGEWKMDRVLWVDKKDKIAKTPKVG
BHL8                                        MAKMKCTWPELVGKTVEKAKKMIMKDKPEAKIMVLPVGTKVTGEWKMDRVRLWVDKKDKIAKTPKCG
BHLX                                        XXXXKXXWPELVGKXVEXAKKXIXXDKPEAXIXVLPVGTXVXXXXXXDXVXLXVDKDXXAXXPXXG
BHLXP                                       XXXXKXXWPELVGKXXEXAKKXIXXDKPXAXIXVLPXGTXVXXXXXXXXVXLXXDKDXXAXXPXXG
                  10        20        30        40        50        60        70        80
                   *         *         *         *         *         *         *         *
```

FOREIGN PATENT DOCUMENTS

WO        WO 95/27088 A1    10/1995

OTHER PUBLICATIONS

Liew et al. (1994) Proc. Natl. Acad. Sci. USA, vol. 91, pp. 10645.*
Han et al. (1988) Nucleic Acids Research, vol. 16, pp. 11837.*
Peterson et al. (1991) Plant Physiol., vol. 96, pp. 1389-1390.*
Roesler and Rao (1999) protein Engineerin, vol. 12, pp. 967-973.*
Burow et al., Suppression of phaseolin and lectin in seeds of common bean, *Phoseolus vulgaris* L.: Increased accumulation of 54 kDa polypeptides is not associated with higher seed methionine concentrations, Mol. Gen. Genet. (1993) 241:431-439.
Karchi et al., Seed-specific expression of a bacterial desensitized aspartate kinase increases the production of seed threonine and methionine in transgenic tobacco, Plant Journal (1993) 3(5):721-727.
Jonassen, I., Characteristics of Hiproly Barley I. Isolation and Characterisation of two Water-Soluble High-Lysine Proteins, Carlsberg Res. Commun. (1980) 45:47-56.
Svendsen et al., Characteristics of Hiproly Barley III. Amino Acid Sequences of Two Lysine-Rich Proteins. Carlsberg Res. Commun. (1980) 45:79-85.
McPhalen et al., Crystal and Molecular Structure of the Serine Proteinase Inhibitor CI-2 from Barley Seeds, Biochemistry (1987) 26(1):261-269.
Clore et al., Comparison of the solution and X-ray structures of barley serine proteinase inhibitor 2, Protein Engineering (1987) 1(4):313-318.
Zabin et al., Approaches to Predicting Effects of Single Amino Acid Substitutions on the Function of a Protein, Biochemistry (1991) 30(25):6230-6240.
Summers et al., A Conservative Amino Acid Substitution, Arginine for Lysine Abolishes Export of a Hybrid Protein in *Escherichia coli*, Journal of Biological Chemistry (1989) 264(33):20062-20068.
Ringe, D., The sheep in wolf's clothing, Nature (1989) 339:656-659.
Hirabayashi et al., Effect of Amino Acid Substitution by Site-directed Mutagenesis of the Carbohydrate Recognition and Stability of human 14-kDA β-Galactoside-binding Lectin, Journal of Biological Chemistry (1991) 266(35):23648-23653.
Van Eijsden et al., Mutational analysis or pea lectin. Substitution of $Asn^{126}$ for Asp in the monosaccharide-binding site climinate mannose/glucose-binding activity, Plant Molecular Biology (1992) 20:1049-1058.
Leatherbarrow et al., Design of a Small Peptide-Based Proteinase Inhibitor by Modeling the Active-Site Region of Barley Chymotrypain Inhibitor 2. Biochemistry (1991) 30(44):10717-10721.
Jackson et al., Contribution of Residues Reactive Site Loop of Chymotrypsin Inhibitor 2 to Protein Stability and Activity, Biochemistry (1994) 33(46):13880-13887.
Jandue et al., Rote of Arginine 67 in the Stabilization of Chymotrypsin Inhibitor 2: Examination of Arnige Proton Exchange Rates and Denaturation Thomodynamics of an Engineered Protein, Biochemistry (1990) 29(26):6264-6289.
Kjaer et al., Sequence Specific Assignment of the Proton Nuclear Magnetic Resonance Spectrum of Barley Serine Proteinase Inhibitor 2, Carlsberg Res. Commun. (1987) 52:327-354.
Rao et al., Synthesis and chracaterization of defensin NP-1, Int. J. Peptide Protein Res. (1992) 40:507-514.
Berry-Lowe et al., The Nucleotide Sequence, Expression, and Evolution of One Member of a Multigene Family Encoding the Small Subunit of Ribulose-1,5-Bisphosphate Carboxylase in Soybean, Journal of Molecular and Applied Genetics (1982) 1(6):483-498.
Cashmore, A.R., Nuclear Genes Encoding the Small Subunit of Ribulose-1,5-Bisphosphate Carboxylase, Genetic Engineering of Plants: An Agricultural Perspective (1983) 29-38.
Coruzzi et al., Nucleotide Sequences of Two Pea cDNA Clones Encoding the Small Subunit of Ribulose 1,5-Bisphosphate Carboxylase and the Major Chlorophyll a/b-binding Thylakoid Polypeptide, Journal of Biological Chemistry (1983) 258(3):1399-1402.
Dunsmuir et al., The Major Chlorophyll a/b Bidning Protein of Patunia Is Composed of Several Polypeptides Encoded by a Number of Distinct Nuclear Genes, Journal of Molecular and Applied Genetics (1983) 2:285-300.
Williamson et al., Nucleotide sequence of barley chymotrypsin inhibitor-2 (CI-2) and its expression in normal and high-lysine barley, Eur. Journal Biochem (1987) 165(1):99-106.
McPhalen et al., Crystal and molecular structure of chymotrypsin inhibitor 2 from barley seeds in complex with subtilisin Navo, Proc. Natl. Acad. Sci. USA (1985) 82:7242-7246.
Cordero, M.J., *Z.mays* mRNA for subtilisin-chymotrypsin inhibitor. EMBL Accession No. X69972 (1995).
Cordero et al., Epression of a maize proteinase inhibitor gene is induced in response to wounding and fungal Infection: systematic wound-response of a monocot gene, Plant Journal (1994) 6(2); 141-150.
Chevalier et al., *Z.maya* mRNA for pis7, EMBL Accession No. X82187 (1994).
Otzen et al., Folding of Circular and Permuted Chymotrypsin Inhibitor 2: Retention of the Folding Nucleus, Biochemistry (1998) 37:8139-8145.
Ladurner et al., Glutamine, Alanine or Glycine Repeats Inserted into the Loop of a Protein Have Minimal Effects on Stability and Folding Rates, J. Mol. Biol. (1997) 273:330-337.
Campbell, A.F., Protein Engineering of the Battery Chymotrypsin Inhibitor 2, Plant Protein Engineering (1992) pp. 257-266.
Kleber-Janke et al., Isolation of cDNA clones for genes showing enhanced expression in barley leaves during dark-induced senesconce as well as during senescence under field conditions, Planta (1997) 203(3):332-340.

* cited by examiner

Figure 1

SEQUENCES OF BHL PROTEINS

```
                         10         20         30         40         50         60         70         80
                          *          *          *          *          *          *          *          *
WT CI - 2 (native) SSVEKKPEGVNTGAGDRHNLKTEWPELVGKSVEEAKKVILQDKPEAQIIVLPVGTIVTMEYRIDRVRLFVDKLDNIAQVPRVG
WT CI-2                            MNLKTEWPELVGKSVEEAKKVILQDKPEAQIIVLPVGTIVTMEYRIDRVRLFVDKLDNIAQVPRVG
BHL1                              MKLKTEWPELVGKSVEKAKKVILKDKPEAQIIVLPVGTKVTKEYKIDRVKLFVDKKDNIAQVPRVG
BHL2                              MKLKTEWPELVGKSVEKAKKVILKDKPEAQIIVLPVGTKVAKAYKIDKVKLFVDKKDNIAQVPRVG
BHL3                              MKLKTEWPELVGKSVEKAKKVILKDKPEAQIIVLPVGTKVGKHYKIDKVKLFVDKKDNIAQVPRVG
BHL3N              MKSVEKKPKGVKTGAGDKHKLKTEWPELVGKSVEKAKKVILKDKPEAQIIVLPVGTKVGKHYKIDKVKLFVDKKDNIAQVPRVG
BHL4                              MKLKTEWPELVGKSVEKAKKVILKDKPEAQIIVLPVGTKVTGEYKIDRVKLFVDKKDNIAQVPRVG
BHL5                              MAKMKTTWPELVGKTVEKAKKMIMKDKPEAKIMVLPVGTKVTGEWKMDRVKLWVDKKDKIAKTPKVG
BHL6                              MAKMKTTWPELVGKTVEKAKKMIMKDKPEAKIMVLPVGTKVTGEWKMDRVRLWVDKKDKIAKTPKVG
BHL8                              MAKMKCTWPELVGKTVEKAKKMIMKDKPEAKIMVLPVGTKVTGEWKMDRVRLWVDKKDKIAKTPKCG
BHLX                         XXXXXXXXWPELVGKXVEXAKKXIXXDKPEAXIXVLPVGTXVXXXXXDXVXLXVDKXDXXAXXPXXG
BHLXP                        XXXXXXXXWPELVGKXXEXAKKKXIXXDKPXAXIXVLPXGTXVXXXXXXXXVXLXXDKXDXXAXXPXXG
                          10         20         30         40         50         60         70         80
                          *          *          *          *          *          *          *          *
```

```
         20          30          40          50          60          70          80
          *           *           *           *           *           *           *
WT CI-2   MNLKTEWPELVGKSVEEAKKVILQDKPEAQIIVLPV-GTIV-TMEYRIDRVLFVDKLDNIAQVPRVG
Homologs
 1        GAKTSWPEVVGMSAEKAKEIILRDKPNAQIEVIPV-DAMV-PLNFNPNRVFVLVHKATTVAZVSRVG
 2        GAKTEWPELVGCTIKEAKEKIKADRPDLKVVIVPV-GSIV-TQEIDLNRVRVWVDKV---AKVPKIG
 3        GAKTSWPEVVGLSVEDAKKVILKDKPDADIVVLPV-GSVV-TADYRPNRVRIFVDIV---AQTPHIG
 4        --RTSWPELVGVSAEEARK-IKEEMPEAEIQVVPQ-DSFV-TADYKFQRVRLYVDESNKVVRAAPIG
 5        AEKSSWPELVGEDGEEAVKIIQQENPSLDVILMPR-GQNWATLDCRPNRVRVFNDESGKVNSIPRIG
 6        TRKTSWPELVGVTAEEAE-KIKEEMSGVEIQVVPP-GSFV-TADYKPQRVRLYVDESNKVTRTPGIG
 7        PTKTSWPELVGVTAEQAETKIKEEMVDVQIQVSPH-DSFV-TADYNPKRVRKYVDESNKVTRTPSIG
 8        VTKERWPELLGTPAKFAMQIIQKENPKLTNVQTVLNGTPV-TEDLRCNRVRLFVNVLDFVVQTPQVG
 9        NKKETWPELIGVPAKFAREIIQKENSKLTNVPSVLNGSPV-TKDFRCERVRLFVNVLDFVVQIPRVG
10        VGKNTWPELCGARGEEAAATVETENPSVTAVIVPE-GSIV-TTDERCDRVRVWVDENGIVTRVPVIG
11        QGKSSWPQLVGSTGAAAKAVIERENPRVRAVIIKV-GSGA-TKDFRCDRVRVWVTERGIVARPPTIG
12        PGKSSWPHLVGVGGSVAKAIIERQNPNVKAVILEE-GTPV-TKDFRCNRVRIWVNKRGLVVSPPRIG
13        DGKLQWPELIGVPTKLAKEIIEKQNSLISNVHILLNGSPV-TMDFRCNRVRLFDDILGSVVQIPRVA
14        NGKLSWPELIGVPAHYAKGIIEKENSLITNVQILLNGSPV-TMDYRCNRVRLFDNILGDVVQIPRVA
15        KGKQFWPELIGVPALYAKGIIEKENPSITNIPILLNGSPV-TKDFRCDRVRLFVNILGDVVQIPRVT
16        VTKESWPELLGTPAKFAKQIIQKENPKLTNVETLLNGSAF-TEDLRCNRVRLFVNLLDIVVQTPKVG
17        EGKQMWPELIGVPTKLAKEIIEKENPSITNIPILLSGSPI-TLDYLCDRVRLFDNILGFVVQMPVVT
18        PGKQEWPELVGEYGYKAAAIIERENPNVRSIVKHE-RSGF-TKDFRCDRVWVVVDSTGVVRTPRVT
19        VIFNSWSVLTGTNGDYAAVVIERENPTVNAAVILD-GSPV-TADFRCDRVRVFVDGNRIVVKTPKSG
```

Figure 2

EXPRESSION CASSETTES FOR PRODUCING PLANTS WITH INCREASED LEVELS OF ESSENTIAL AMINO ACIDS

CROSS-REFERENCE TO RELATED APPLICATIONS

This application claims priority from and is a continuation of U.S. patent application Ser. No. 09/311,689 now U.S. Pat. No. 6,800,726 which is a continuation-in-part of U.S. patent application Ser. No. 08/740,682 filed Nov. 1, 1996, now abandoned; this application also claims priority from U.S. patent application Ser. No. 09/297,418 filed Apr. 30, 1999, now abandoned, which claims priority from PCT/US97/20441, filed Oct. 31, 1997.

U.S. patent application Ser. No. 08/740,682, U.S. patent application Ser. No. 09/297,418 and PCT/US97/20441 are incorporated by reference herewithin.

FIELD OF THE INVENTION

The present invention relates to the field of protein engineering wherein changing amino acid compositions effects improvements in the nutrition content of feed and food. Specifically, the present invention relates to methods of enhancing the nutritional content of animal feed by expressing derivatives of a protease inhibitor to provide higher percentages of essential amino acids in plants.

BACKGROUND OF THE INVENTION

Feed formulations are required to provide animals essential nutrients critical to growth. However, crop plants are generally rendered food sources of poor nutritional quality because they contain low proportions of several amino acids which are essential for, but cannot be synthesized by, monogastric animals.

For many years researchers have attempted to improve the balance of essential amino acids in the seed proteins of important crops through breeding programs. As more becomes known about seed storage proteins and the expression of the genes which encode these proteins, and as transformation systems are developed for a greater variety of plants, molecular approaches for improving the nutritional quality of seed proteins can provide alternatives to the more conventional approaches. Thus, specific amino acid levels can be enhanced in a given crop via biotechnology.

One alternative method is to express a heterologous protein of favorable amino acid composition at levels sufficient to obviate feed supplementation. For example, a number of seed proteins rich in sulfur amino acids have been identified. A key to good expression of such proteins involves efficient expression cassettes with tissue-preferred promoters. Not only must the gene-controlling regions direct the synthesis of high levels of mRNA, the mRNA must be translated into a stable protein and over-expression of this protein must not be detrimental to plant or animal health.

Among the essential amino acids needed for animal nutrition, often limiting in crop plants, are methionine, threonine, lysine, isoleucine, leucine, valine, tryptophan, phenylalanine, and histidine. Attempts to increase the levels of these free amino acids by breeding, mutant selection and/or changing the composition of the storage proteins accumulated in crop plants has met with limited success.

A transgenic example is the phaseolin-promoted Brazil nut 2S expression cassette. However, even though Brazil nut protein increases the amount of total methionine and bound methionine, thereby improving nutritional value, there appeared to be a threshold limitation as to the total amount of methionine that is accumulated in the seeds. The seeds remain insufficient as sources of methionine and methionine supplementation is required in diets utilizing soybeans.

An alternative to the enhancement of specific amino acid levels by altering the levels of proteins containing the desired amino acid is modification of amino acid biosynthesis. Recombinant DNA and gene transfer technologies have been applied to alter enzyme activity catalyzing key steps in the amino acid biosynthetic pathway. See Glassman, U.S. Pat. No. 5,258,300; Galili, et al., European Patent Application No. 485970; (1992); incorporated herein in its entirety. However, modification of the amino acid levels in seeds is not always correlated with changes in the level of proteins that incorporate those amino acids. See Burrow, et al., Mol. Gen. Genet.; Vol. 241; pp. 431–439; (1993); incorporated herein in its entirety by reference. 1 Increases in free lysine levels in leaves and seeds have been obtained by selection for DHDPS mutants or by expressing the E. coli DHDPS in plants. However, since the level of free amino acids in seeds, in general, is only a minor fraction of the total amino acid content, these increases have been insufficient to significantly increase the total amino acid content of seed.

The lysC gene is a mutant bacterial aspartate kinase which is desensitized to feedback inhibition by lysine and threonine. Expression of this gene results in an increase in the level of lysine and threonine biosynthesis. However, expression of this gene with seed-specific expression cassettes has resulted in only a 6–7% increase in the level of total threonine or lysine in the seed. See Karchi et al., The Plant J.; Vol. 3; pp. 721–7; (1993); incorporated herein in its entirety by reference. Thus, there is minimal impact on the nutritional value of seeds, and supplementation with essential amino acids is still required.

In another study (Falco et al., Biotechnology 13:577–582, 1995), manipulation of bacterial DHDPs and aspartate kinase did result in useful increases in free lysine and total seed lysine. However, abnormal accumulation of lysine catabolites was also observed suggesting that the free lysine pool was subject to catabolism.

Based on the foregoing, there exists a need for methods of increasing the levels of essential amino acids in seeds of plants. Previous approaches have led to insufficient increases in the levels of both free and bound amino acids and insignificant enhancement of the nutritional content of the feed.

SUMMARY OF THE INVENTION

It is the object of the present invention to provide nucleic acids and polypeptides relating to the enhancement of essential amino acids in plants.

It is another object of the present invention to provide antigenic fragments of the polypeptides of the present invention.

It is another object of the present invention to provide transgenic plants comprising the nucleic acids of the present invention.

It is another object of the present invention to provide methods making and expressing, in a transgenic plant, of the nucleic acids of the present invention.

It is another object that expression of the nucleic acids encoding the proteins of the present invention can be increased relative to a non-transformed control plant.

It is an object to provide a digestible substituted protein.

It is an object to provide a proteotypically stable, substituted protein, able to accumulate to useful levels in plants.

It is an object of this invention to provide a polypeptide with a non-native residue in more than about 11% to less than about 75% of the amino acid residues.

It is therefore an object of the present invention to provide methods for increasing the levels of one or more of a combination of essential amino acid in the seeds of plants used for animal feed.

It is a further object of the present invention to provide seeds for food and/or feed with higher levels of essential amino acid, than wild type species of the same seeds.

It is a further object of the present invention to provide seeds for food and/or feed such that the level of one or more of the essential amino acids is increased such that the need for feed supplementation is greatly reduced or obviated.

It is an object of the present invention to provide a CI-2-like polypeptide with an increased level of essential amino acids through substitution of seven or more of the amino acid residues in a CI-2-like polypeptide. Seven or more of positions 1, 8, 11, 17, 18, 19, 20, 22, 23, 31, 34, 38, 40, 41, 47, 49, 56, 58, 59, 60, 61, 62, 63, 65, 67, 69, 73, 75, 76, 78, 79, 81, 82, or combinations thereof.

of the wild type protein are substituted with essential amino acid.

It is an object of the present invention to provide expression of the present chymotrypsin inhibitor derivatives in plants to provide higher percentages of essential amino acid in plants than wild type plants.

It is an object of this invention to provide a CI-2-like polypeptide with increased stability.

It is an object of the present invention to provide methods for increasing the essential amino acid content of plants.

It is an object of the present invention to provide methods for increasing the nutritional value of a protein by altering a CI-2-like polypeptide to enhance its nutritional value by substituting essential amino acids at positions corresponding to 1, 8, 11, 17, 18, 19, 20, 22, 23, 31, 34, 38, 40, 41, 47, 49, 56, 58, 59, 60, 61, 62, 63, 65, 67, 69, 73, 75, 76, 78, 79, 81, 82, or combinations thereof.

DETAILED DESCRIPTION OF THE INVENTION

Choices of substitutions described herewithin are optionally grouped within parentheses and are separated by a semicolon. The native amino acid precedes the position number using SEQ ID NO. 2 as a reference. The possible substitutions follow the residue number.

Sequence Identification

Full length wild-type chymotrypsin inhibitor (WT CI-2) is coded for by the polypeptides of SEQ ID No. 2 which is encoded for by the nucleic acid of SEQ ID No. 1.

Truncated wild-type chymotrypsin inhibitor (WT CI-2) is coded for by the polypeptides of SEQ ID No. 4 which is encoded for by the nucleic acid of SEQ ID No. 3.

Barley High Lysine 1(BHL1) is coded for by the polypeptides of SEQ ID No. 6 which is encoded for by the nucleic acid of SEQ ID No. 5.

Barley High Lysine 2 (BHL2) is coded for by the polypeptides of SEQ ID No. 8 which is encoded for by the nucleic acid of SEQ ID No. 7.

Barley High Lysine 3 (BHL3) is coded for by the polypeptides of SEQ ID No. 10 which is encoded for by the nucleic acid of SEQ ID No. 9.

Barley High Lysine 3N (BHL3N) is coded for by the polypeptides of SEQ ID No. 12 which is encoded for by the nucleic acid of SEQ ID No. 11.

Barley High Lysine 4 (BHL4) is coded for by the polypeptides of SEQ ID No. 14 which is encoded for by the nucleic acid of SEQ ID No. 13.

Barley High Lysine 5 (BHL5) is coded for by the polypeptides of SEQ ID No. 16 which is encoded for by the nucleic acid of SEQ ID No. 15.

Barley High Lysine 6 (BHL6) is coded for by the polypeptides of SEQ ID No. 8 which is encoded for by the nucleic acid of SEQ ID No. 17.

Barley High Lysine 8 (BHL8) is coded for by the polypeptides of SEQ ID No. 20 which is encoded for by the nucleic acid of SEQ ID No. 19.

The 5' and 3' PCR primer pairs A & B, are identified as SEQ ID Nos. 21 and 22, respectively.

Maize EST PI-1 is coded for by the polypeptides of SEQ ID No.24 which is encoded for by the nucleic acid of SEQ ID No. 23.

Maize EST PI-2 is coded for by the polypeptides of SEQ ID No.26 which is encoded for by the nucleic acid of SEQ ID No. 25.

Maize EST PI-3 is coded for by the polypeptides of SEQ ID No.28 which is encoded for by the nucleic acid of SEQ ID No. 27.

Maize EST PI-4 is coded for by the polypeptides of SEQ ID No. 30 which is encoded for by the nucleic acid of SEQ ID No. 29.

Maize EST PI-5 is coded for by the polypeptides of SEQ ID No. 32 which is encoded for by the nucleic acid of SEQ ID No. 31.

It has been unexpectedly discovered that one class of compounds, derivatives of chymotrypsin inhibitor-2 ("CI-2"), can be modified to enhance its essential amino acid content. In a preferred embodiment of the present invention, the CI-2 derivatives simultaneously exhibit both enhanced essential amino acids. The present compounds are thus excellent candidates for feed grain and food transformation to enhance nutrition.

Definitions

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

A "CI-2 derived" polypeptide refers to a chymotrypsin inhibitor polypeptide that may be truncated or modified, substituted or have an amino terminal extension or an insert.

A "CI-2 like" polypeptide refers to a polypeptide of at least 23 consecutive amino acids of Seq. ID No. 2 or 4; or a polypeptide of at least 30% amino acid sequence identity with corresponding region of Seq. ID Nos. 2 or 4 or 20; or a CI-2-like polypeptide with modifications identified in CI-2; or a protease inhibitor with an active site loop typically between 53 and 70; or a CI-2 homologue modified to enhance its nutritional value by altering the amino acid residues at positions corresponding to those defined herein. The gene sequences from the following organisms (cited by Genebank Accession Numbers) may be modified according to the methods in the specification: *Hordeum vulgare* (A01293), *Hordeum vulgare* (Y08625), *Zea mays* (S37493), *Vicia faba* (A21463), *Cucurbita maxima* (S55591, S12897), Canavalia lineata (JC2380), *Vigna* angularis (JX0089), *Nicotiana tabacum* (S33547), *Nicotiana sylvestris* (A56555), *Sambucus nigra* (Z46949), *Momordica charantia* (JC2508), *Cucurbita maxima* (S12897), *Solanum tuberosum* (A01291, U30861), *Solanum tuberosum* (U30861), *Lycopersicon peruvianum* (A39547), *Lycopersicon esculentum* (A32067, A24048), *Lycopersicon esculentum* (A24048), *Amaranthus caudatus* (S40496), *Arabidopsis thalania* (AC005770).

"Nutritionally-enhancing" refers to adding nutritional components that could include essential amino acids, fat, oil, and or vitamins and other compositions imparting characteristics desired in feed.

"%" refers to molar % unless otherwise specified or implied.

"Essential amino acids" are amino acids that must be obtained from an external source because they are not synthesized by the individual. They are: methionine, threonine, lysine, isoleucine, leucine, valine, tryptophan, phenylalanine, and histidine.

The term "antibody" includes reference to antigen binding forms of antibodies (e.g., Fab, F(ab)$_2$). The term "antibody" refers to a polypeptide substantially encoded by an immunoglobulin gene or immunoglobulin genes, or fragments thereof which specifically bind and recognize an analyte (antigen). While various antibody fragments are defined in terms of the digestion of an intact antibody, one of skill will appreciate that such fragments may be synthesized de novo either chemically or by utilizing recombinant DNA methodology.

The term "conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein which encodes a polypeptide also describes every possible silent variation of the nucleic acid. One of ordinary skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide of the present invention is implicit in each described polypeptide sequence and incorporated herein by reference.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for it's native substrate. Conservative substitution tables providing functionally similar amino acids are well known in the art.

The following six groups each contain amino acids that are conservative substitutions for one another:
1) Alanine (A), Serine (S), Threonine (T), Cysteine (C);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W.H. Freeman and Company.

The following groups each contain amino acids that are conservative and essential amino acid substitutions for one another:
1) Threonine(T), and Lysine (K)
2) Isoleucine (I), Leucine (L), Methionine (M), and Valine (V).

The term "isolated" refers to material, such as a nucleic acid or a protein, which is: (1) substantially or essentially free from components which normally accompany or interact with the material as found in its naturally occurring environment or (2) if the material is in its natural environment, the material has been altered by deliberate human intervention to a composition and/or placed at a locus in the cell other than the locus native to the material.

As used herein, "polypeptide" means proteins, protein fragments, modified proteins, amino acid sequences and synthetic amino acid sequences. The polypeptide can be glycosylated or not.

As used herein, "plant" includes but is not limited to plant cells, plant tissue and plant seeds.

As used herein, "promoter" includes reference to a region of DNA upstream from the start of transcription and involved in recognition and binding of RNA polymerase and other proteins to initiate transcription.

By "fragment" is intended a portion of the nucleotide sequence or a portion of the amino acid sequence and hence protein encoded thereby. Preferably fragments of a nucleotide sequence may encode protein fragments that retain the biological activity of the native nucleic acid. However, fragments of a nucleotide sequence which are useful as hybridization probes generally do not encode fragment proteins retaining biological activity. Fragments of a nucleotide sequence are generally greater than 10 nucleotides, preferably at least 20 nucleotides and up to the entire nucleotide sequence encoding the proteins of the invention. Generally probes are less than 1000 nucleotides and preferably less than 500 nucleotides. Fragments of the invention include antisense sequences used to decrease expression of the inventive nucleic acids. Such antisense fragments may vary in length ranging from at least about 20 nucleotides, about 50 nucleotides, about 100 nucleotides, up to and including the entire coding sequence.

By "variants" is intended substantially similar sequences. Generally, nucleic acid sequence variants of the invention will have at least 40%, 50%, 55%, 60%, 70%, or preferably 80%, more preferably at least 90% and most preferably at least 95% sequence identity to the native nucleotide sequence.

Generally, polypeptide sequence variants of the invention will have at least about 55%, 60%, 70%, 80%, or preferably at least about 90% and more preferably at least about 95% sequence identity to the modified protein.

As used herein, "sequence identity" or "identity" in the context of two nucleic acid or polypeptide sequences includes reference to the residues in the two sequences that are the same when aligned for maximum correspondence over a specified comparison window. An indication that two peptide sequences are substantially identical is that one peptide is immunologically reactive with antibodies raised against the second peptide. A polypeptide is substantially identical to a second polypeptide, for example, where the two polypeptides differ only by conservative substitution.

Methods of alignment of sequences for comparison are well-known in the art. For purposes of defining the present invention, the BLAST 2.0 suite of programs using default parameters is used. Altschul et al., *Nucleic Acids Res.* 25:3389–3402 (1997). Software for performing BLAST analyses is publicly available, e.g., through the National Center for Biotechnology Information (http://www.ncbi.nlm.nih.gov/).

By "functionally equivalent" is intended that the sequence of the variant defines a chain that produces a protein having substantially the same biological effect as the native protein of interest.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17: 477–498 (1989)). Thus, the maize preferred codon for a particular amino acid may be derived from known gene sequences from maize. Maize codon usage for 28 genes from maize plants are listed in Table 4 of Murray et al., supra.

By "immunologically reactive conditions" is meant conditions which allow an antibody, generated to a particular epitope, to bind to that epitope to a detectably greater degree (e.g., at least 2-fold over background) than the antibody binds to substantially all other epitopes. Immunologically reactive conditions are dependent upon the format of the antibody binding reaction and typically are those utilized in immunoassay protocols. See Harlow and Lane, *Antibodies, A Laboratory Manual*, Cold Spring Harbor Publications, New York (1988), for a description of immunoassay formats and conditions.

The terms "isolated" or "biologically pure" refer to material which is: (1) substantially or essentially free from components which normally accompany or interact with it as found in its naturally occurring environment. The isolated material optionally comprises material not found with the material in its natural environment.

(2) If the material is in its natural environment, the material has been synthetically (non-naturally) altered to a composition and/or placed at a locus in the cell (e.g., genome) not native to a material found in that environment. The alteration to yield the synthetic material can be performed on the material within or removed from its natural state. For example, a naturally occurring nucleic acid becomes an isolated nucleic acid if it is altered, or if it is transcribed from DNA which is altered, by non-natural, synthetic (i.e., "man-made") methods performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (e.g., a promoter) become isolated if it is introduced by non-naturally occurring means to a locus of the genome not native to that nucleic acid.

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds, suspension cultures, embryos, meristematic regions, callus tissue, leaves, roots, shoots, gametophytes, sporophytes, pollen, and microspores. The class of plants which can be used in the methods of the invention is generally as broad as the class of higher plants amenable to transformation techniques, including both monocotyledonous and dicotyledonous plants. Particularly preferred is *Zea mays*.

As used herein, "polynucleotide" includes reference to a deoxyribopolynucleotide, ribopolynucleotide, or analogs thereof, that hybridize to nucleic acids in a manner similar to naturally occurring nucleotides. A polynucleotide can be full-length or a sub-sequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. Among the known modifications which may be present in polypeptides of the present are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance *Proteins—Structure and Molecular Properties,* 2nd ed., T. E. Creighton, W. H. Freeman and Company, New York (1993). Many detailed reviews are available on this subject, such as, for example, those provided by Wold, F., Posttranslational Protein Modifications: Perspectives and Prospects, pp. 1–12 in *Posttranslational Covalent Modification of Proteins,* B. C. Johnson, Ed., Academic Press, New York (1983); Seifter et al., Meth. Enzymol. 182: 626–646 (1990) and Rattan et al., *Protein Synthesis: Posttranslational Modifications and Aging,* Ann. N.Y. Acad. Sci. 663: 48–62 (1992). It will be appreciated, as is well known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli* or other cells, prior to proteolytic processing, almost invariably will be N-formylmethionine. During post-translational modification of the peptide, a methionine residue at the $NH_2$-terminus may be deleted. Accordingly, this invention contemplates the use of both the methionine-containing and the methionineless amino terminal variants of the protein of the invention. In general, as used herein, the term polypeptide encompasses all such modifications, particularly those that are present in polypeptides synthesized by expressing a polynucleotide in a host cell.

The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, more preferably at least 70%, 80%, 90%, and most preferably at least 95%. Polypeptides which are "substantially similar" share sequences as noted above except that residue positions which are not identical may differ by conservative amino acid changes.

Nucleic Acids

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a monocot or dicot. In preferred embodiments the monocot is corn, sorghum, barley, wheat, millet, or rice. Preferred dicots include soybeans, sunflower, canola, alfalfa, cotton, potato, lupin or cassaya.

Functional fragments included in the invention can be obtained using primers that selectively hybridize under stringent conditions. Primers are generally at least 12 bases in length and can be as high as 200 bases, but will generally be from 15 to 75, preferably from 15 to 50. Functional fragments can be identified using a variety of techniques such as restriction analysis, Southern analysis, primer extension analysis, and DNA sequence analysis.

The present invention includes a plurality of polynucleotides that encode for the identical amino acid sequence. The degeneracy of the genetic code allows for such "silent variations" which can be used, for example, to selectively hybridize and detect allelic variants of polynucleotides of the present invention. Additionally, the present invention includes isolated nucleic acids comprising allelic variants. The term "allele" as used herein refers to a related nucleic acid of the same gene.

Variants of nucleic acids included in the invention can be obtained, for example, by oligonucleotide-directed mutagenesis, linker-scanning mutagenesis, mutagenesis using the polymerase chain reaction, and the like. See, for example, Ausubel, pages 8.0.3–8.5.9. Also, see generally, McPherson (ed.), *DIRECTED MUTAGENESIS: A Practical approach,* (IRL Press, 1991). Thus, the present invention also encompasses DNA molecules comprising nucleotide sequences that have substantial sequence similarity with the inventive sequences.

Variants included in the invention may contain individual substitutions, deletions or additions to the nucleic acid or polypeptide sequences. Such changes will alter, add or delete a single amino acid or a small percentage of amino acids in the encoded sequence. Variants are referred to as "conservatively modified variants" where the alteration results in the substitution of an amino acid with a chemically similar amino acid. When the nucleic acid is prepared or altered synthetically, advantage can be taken of known codon preferences of the intended host.

The present invention also includes the use of 5' and/or 3' UTR regions for modulation of translation of heterologous coding sequences. Positive sequence motifs include translational initiation consensus sequences (Kozak, *Nucleic Acids Res.* 15:8125 (1987)) and the 7-methylguanosine cap structure (Drummond et al., Nucleic Acids Res. 13:7375 (1985)). Negative elements include stable intramolecular 5' UTR stem-loop structures (Muesing et al., *Cell* 48:691 (1987)) and AUG sequences or short open reading frames preceded by an appropriate AUG in the 5' UTR (Kozak, supra, Rao et al., *Mol. and Cell. Biol.* 8:284 (1988)).

Further, the polypeptide-encoding segments of the polynucleotides of the present invention can be modified to alter codon usage. Altered codon usage can be employed to alter translational efficiency and/or to optimize the coding sequence for expression in a desired host or to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group (see Devereaux et al., *Nucleic Acids Res.* 12: 387–395 (1984)) or MacVector 4.1 (Eastman Kodak Co., New Haven, Conn.).

For example, the inventive nucleic acids can be optimized for enhanced expression in organisms of interest. See, for example, EPA0359472; WO91/16432; Perlak et al. (1991) *Proc. Natl. Acad. Sci. USA* 88:3324–3328; and Murray et al. (1989) *Nucleic Acids Res.* 17:477–498. In this manner, the genes can be synthesized utilizing species-preferred codons. See, for example, Murray et al. (1989) *Nucleic Acids Res.* 17:477–498, the disclosure of which is incorporated herein by reference.

The present invention provides subsequences comprising isolated nucleic acids containing at least 16 contiguous bases of the inventive sequences. For example the isolated nucleic acid includes those comprising at least 20, 25, 30, 40, 50, 60, 75 or 100 contiguous nucleotides of the inventive sequences. Subsequences of the isolated nucleic acid can be used to modulate or detect gene expression by introducing into the subsequences compounds which bind, intercalate, cleave and/or crosslink to nucleic acids.

The nucleic acids of the invention may conveniently comprise a multi-cloning site comprising one or more endonuclease restriction sites inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention.

A polynucleotide of the present invention can be attached to a vector, adapter, promoter, transit peptide or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known and extensively described in the art. For a description of such nucleic acids see, for example, Stratagene Cloning Systems, Catalogs 1995, 1996, 1997 (La Jolla, Calif.); and, Amersham Life Sciences, Inc, Catalog '97 (Arlington Heights, Ill.).

The isolated nucleic acid compositions of this invention, such as RNA, cDNA, genomic DNA, or a hybrid thereof, can be obtained from plant biological sources using any number of cloning methodologies known to those of skill in the art. In some embodiments, oligonucleotide probes which selectively hybridize, under stringent conditions, to the polynucleotides of the present invention are used to identify the desired sequence in a cDNA or genomic DNA library.

Exemplary total RNA and mRNA isolation protocols are described in Plant *Molecular Biology: A Laboratory Manual*, Clark, Ed., Springer-Verlag, Berlin (1997); and, *Current Protocols in Molecular Biology*, Ausubel et al., Eds., Greene Publishing and Wiley-Interscience, New York (1995). Total RNA and mRNA isolation kits are commercially available from vendors such as Stratagene (La Jolla, Calif.), Clonetech (Palo Alto, Calif.), Pharmacia (Piscataway, N.J.), and 5'-3' (Paoli, Pa.). See also, U.S. Pat. Nos. 5,614,391; and, 5,459,253.

Typical cDNA synthesis protocols are well known to the skilled artisan and are described in such standard references as: *Plant Molecular Biology: A Laboratory Manual*, Clark, Ed., Springer-Verlag, Berlin (1997); and, *Current Protocols in Molecular Biology*, Ausubel et al., Eds., Greene Publishing and Wiley-Interscience, New York (1995). cDNA synthesis kits are available from a variety of commercial vendors such as Stratagene or Pharmacia.

Typically, stringent hybridization conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

Preferably the hybridization is conducted under low stringency conditions which include hybridization with a buffer solution of 30% formamide, 1 M NaCl, 1% SDS (sodium dodecyl sulfate) at 37° C. for 24 hrs., and a wash in 1× to 2×SSC (20×SSC=3.0 M NaCl/0.3 M trisodium citrate) at 50° C. More preferably the hybridization is conducted under moderate stringency conditions which include hybridization in 40% formamide, 1 M NaCl, 1% SDS at 37° C. for 24 hrs., and a wash in 0.5× to 1×SSC at 55° C. Most preferably the hybridization is conducted under high stringency conditions which include hybridization in 50% formamide, 1 M NaCl, 1% SDS at 37° C. for 24 hrs., and a wash in 0.1×SSC at 60° C.

An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y. (1993); and *Current Protocols in Molecular Biology*, Chapter 2, Ausubel, et al., Eds., Greene Publishing and Wiley-Interscience, New York (1995). Often, cDNA libraries will be normalized to increase the representation of relatively rare cDNAs.

The nucleic acids of the invention can be amplified from nucleic acid samples using amplification techniques. For instance, polymerase chain reaction (PCR) technology can be used to amplify the sequences of polynucleotides of the present invention and related genes directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Examples of techniques useful for in vitro amplification methods are found in Berger, Sambrook, and Ausubel, as well as Mullis et al., U.S. Pat. No. 4,683,202 (1987); and, *PCR Protocols A Guide to Methods and Applications*, Innis et al., Eds., Academic Press Inc., San Diego, Calif. (1990). Commercially available kits for genomic PCR amplification are known in the art. See, e.g., Advantage-GC Genomic PCR Kit (Clontech). The T4 gene 32 protein (Boehringer Mannheim) can be used to improve yield of long PCR products.

PCR-based screening methods have also been described. Wilfinger et al. describe a PCR-based method in which the longest cDNA is identified in the first step so that incomplete clones can be eliminated from study. *BioTechniques,* 22(3): 481–486 (1997).

In one aspect of the invention, nucleic acids can be amplified from a *Zea mays* nucleic acid library. The nucleic acid library may be a cDNA library, a genomic library, or a library generally constructed from nuclear transcripts at any stage of intron processing.

Libraries can be made from a variety of maize tissues. Good results have been obtained using mitotically active tissues such as shoot meristems, shoot meristem cultures, embryos, callus and suspension cultures, immature ears and tassels, and young seedlings. The cDNA of the present invention was obtained from developing endosperm. Since cell cycle proteins are typically expressed at specific cell cycle stages it may be possible to enrich for such rare messages using exemplary cell cycle inhibitors such as aphidicolin, hydroxyurea, mimosine, and double-phosphate starvation methods to block cells at the G1/S boundary. Cells can also be blocked at this stage using the double phosphate starvation method. Hormone treatments that stimulate cell division, for example cytokinin, would also increase expression of the cell cycle RNA.

Alternatively, the sequences of the invention can be used to isolate corresponding sequences in other organisms, particularly other plants, more particularly, other monocots. In this manner, methods such as PCR, hybridization, and the like can be used to identify such sequences having substantial sequence similarity to the sequences of the invention. See, for example, Sambrook et al. (1989) *Molecular Cloning: A Laboratory Manual* (2d ed., Cold Spring Harbor Laboratory Press, Plainview, N.Y.). and Innis et al. (1990), *PCR Protocols: A Guide to Methods and Applications* (Academic Press, New York). Coding sequences isolated based on their sequence identity to the entire inventive coding sequences set forth herein or to fragments thereof are encompassed by the present invention.

The isolated nucleic acids of the present invention can also be prepared by direct chemical synthesis by methods such as the phosphotriester method of Narang et al., *Meth. Enzymol.* 68:90–99 (1979); the phosphodiester method of Brown et al., *Meth. Enzymol.* 68:109–151 (1979); the diethylphosphoramidite method of Beaucage et al., *Tetra. Leff.* 22:1859–1862 (1981); the solid phase phosphoramidite triester method described by Beaucage and Caruthers, *Tetra. Letts.* 22(20):1859–1862 (1981), e.g., using an automated synthesizer, e.g., as described in Needham-VanDevanter et al., *Nucleic Acids Res.*, 12: 6159–6168 (1984); and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is limited to sequences of about 100 bases, longer sequences may be obtained by the ligation of shorter sequences.

Expression Cassettes

In another embodiment expression cassettes comprising isolated nucleic acids of the present invention are provided. An expression cassette will typically comprise a polynucleotide of the present invention operably linked to transcriptional initiation regulatory sequences which will direct the transcription of the polynucleotide in the intended host cell, such as tissues of a transformed plant.

The construction of expression cassettes that can be employed in conjunction with the present invention is well known to those of skill in the art in light of the present disclosure. See, e.g., Sambrook et al.; Molecular Cloning: A Laboratory Manual; Cold Spring Harbor, N.Y.; (1989); Gelvin et al.; Plant Molecular Biology Manual; (1990); Plant Biotechnology: Commercial Prospects and Problems, eds. Prakash et al.; Oxford & IBH Publishing Co.; New Delhi, India; (1993); and Heslot et al.; Molecular Biology and Genetic Engineering of Yeasts; CRC Press, Inc., USA; (1992); each incorporated herein in its entirety by reference.

For example, plant expression vectors may include (1) a cloned plant nucleic acid under the transcriptional control of 5' and 3' regulatory sequences and (2) a dominant selectable marker. Such plant expression vectors may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal.

Constitutive, tissue-preferred or inducible promoters can be employed. Examples of constitutive promoters include the cauliflower mosaic virus (CaMV) 35S transcription initiation region, the 1'- or 2'-promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, the GRP1-8 promoter and other transcription initiation regions from various plant genes known to those of skill.

An efficient plant promoter that may be used is an overproducing plant promoter. Overproducing plant promoters that may be used in this invention include the promoter of the chlorophyll $\alpha$-$\beta$ binding protein, and the promoter of the small sub-unit (ss) of the ribulose-1,5-biphosphate carboxylase from soybean. See e.g. Berry-Lowe et al., J. Molecular and App. Gen.; Vol. 1; pp. 483–498; (1982); incorporated herein in its entirety by reference. These two promoters are known to be light-induced, in eukaryotic plant cells. See e.g., An Agricultural Perspective, A. Cashmore, Pelham, N.Y., 1983, pp. 29–38, G. Coruzzi et al., J. Biol. Chem., Vol. 258; p. 1399 (1983), and P. Dunsmuir, et al., J. Molecular and App. Gen., Vol. 2; p. 285 (1983); all incorporated herein in their entirety by reference.

Examples of inducible promoters are the Adh1 promoter which is inducible by hypoxia or cold stress, the Hsp70 promoter which is inducible by heat stress, and the PPDK promoter which is inducible by light. Also useful are promoters which are chemically inducible.

Examples of promoters under developmental control include promoters that initiate transcription preferentially in certain tissues, such as leaves, roots, fruit, seeds, or flowers. An exemplary promoter is the anther specific promoter 5126 (U.S. Pat. Nos. 5,689,049 and 5,689,051). Examples of seed-preferred promoters include, but are not limited to, 27 kD gamma zein promoter and waxy promoter, Boronat, A., Martinez, M. C., Reina, M., Puigdomenech, P. and Palau, J.; Isolation and sequencing of a 28 kD glutelin-2 gene from maize: Common elements in the 5' flanking regions among zein and glutelin genes; Plant Sci. 47, 95–102 (1986) and Reina, M., Ponte, I., Guillen, P., Boronat, A. and Palau, J., Sequence analysis of a genomic clone encoding a Zc2 protein from *Zea mays* W64 A, Nucleic Acids Res. 18 (21), 6426 (1990). See the following site relating to the waxy promoter: Kloesgen, R. B., Gierl, A., Schwarz-Sommer, ZS. and Saedler, H., Molecular analysis of the waxy locus of *Zea mays*, Mol. Gen. Genet. 203:237–244 (1986). Promoters that express in the embryo, pericarp, and endosperm are disclosed in U.S. applications Ser. No. 60/097,233 filed Aug. 20, 1998 and 60/098,230 filed Aug. 28, 1998. The disclosures each of these are incorporated herein by reference in their entirety.

Either heterologous or non-heterologous (i.e., endogenous) promoters can be employed to direct expression of the nucleic acids of the present invention. These promoters can also be used, for example, in expression cassettes to drive expression of antisense nucleic acids to reduce, increase, or alter concentration and/or composition of the proteins of the present invention in a desired tissue.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates. See for example Buchman and Berg, Mol. Cell Biol. 8: 4395–4405 (1988); Callis et al., *Genes Dev.* 1: 1183–1200 (1987). Use of maize introns Adh1-S intron 1, 2, and 6, the Bronze-1 intron are known in the art. See generally, *The Maize Handbook*, Chapter 116, Freeling and Walbot, Eds., Springer, N.Y. (1994).

The vector comprising the sequences from a polynucleotide of the present invention will typically comprise a marker gene which confers a selectable phenotype on plant cells. Usually, the selectable marker gene will encode antibiotic or herbicide resistance. Suitable genes include those coding for resistance to the antibiotic spectinomycin or streptomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance.

Suitable genes coding for resistance to herbicides include those which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), those which act to inhibit action of glutamine synthase, such as phosphinothricin or basta (e.g., the bar gene), or other such genes known in the art. The bar gene encodes resistance to the herbicide basta and the ALS gene encodes resistance to the herbicide chlorsulfuron.

Typical vectors useful for expression of nucleic acids in higher plants are well known in the art and include vectors derived from the tumor-inducing (Ti) plasmid of *Agrobacterium tumefaciens* described by Rogers et al., Meth. In Enzymol., 153:253–277 (1987). Exemplary *A. tumefaciens* vectors useful herein are plasmids pKYLX6 and pKYLX7 of Schardl et al., Gene, 61:1–11 (1987) and Berger et al., Proc. Natl. Acad. Sci. U.S.A., 86:8402–8406 (1989). Another useful vector herein is plasmid pBI101.2 that is available from Clontech Laboratories, Inc. (Palo Alto, Calif.).

A variety of plant viruses that can be employed as vectors are known in the art and include cauliflower mosaic virus (CaMV), *geminivirus*, brome mosaic virus, and tobacco mosaic virus.

Proteins

Proteins of the present invention include proteins derived from the native protein by deletion (so-called truncation), addition, or substitution of one or more amino acids at one or more sites in the native protein. Methods for such deletions, additions and substitutions are generally known in the art.

For example, amino acid sequence variants of the polypeptide can be prepared by mutations in the cloned DNA sequence encoding the native protein of interest. Methods for mutagenesis and nucleotide sequence alterations are well known in the art. See, for example, Walker and Gaastra, eds. (1983) *Techniques in Molecular Biology* (MacMillan Publishing Company, New York); Kunkel (1985) *Proc. Natl. Acad. Sci. USA* 82:488–492; Kunkel et al. (1987) *Methods Enzymol.* 154:367–382; Sambrook et al. (1989) *Molecular Cloning: A Laboratory Manual* (Cold Spring Harbor, N.Y.); U.S. Pat. No. 4,873,192; and the references cited therein; herein incorporated by reference.

In constructing variants of the proteins of interest, modifications to the nucleotide sequences encoding the variants will be made such that variants continue to possess the desired activity. Obviously, any mutations made in the DNA encoding the variant protein must not place the sequence out of reading frame and preferably will not create complementary regions that could produce secondary mRNA structure. See EP Patent Application Publication No. 75,444.

The isolated proteins of the present invention include a polypeptide comprising at least 23 contiguous amino acids encoded by any one of the nucleic acids of the present invention, or polypeptides which are conservatively modified variants thereof. The proteins of the present invention or variants thereof can comprise any number of contiguous amino acid residues from a polypeptide of the present invention, wherein that number is selected from the group of integers consisting of from 23 to the number of residues in a full-length polypeptide of the present invention. Optionally, this subsequence of contiguous amino acids is at least 25, 30, 35, or 40 amino acids in length, often at least 50, 60, 70, 80, or 90 amino acids in length.

The present invention includes modifications that can be made to an inventive protein to increase nutritional enhancement activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

A protein of the present invention can be expressed in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

Typically, an intermediate host cell will be used in the practice of this invention to increase the copy number of the cloning vector. With an increased copy number, the vector containing the nucleic acid of interest can be isolated in significant quantities for introduction into the desired plant cells.

Host cells that can be used in the practice of this invention include prokaryotes, including bacterial hosts such as *Escherichia coli, Salmonella typhimurium*, and *Serratia marcescens*. Eukaryotic hosts such as yeast or filamentous fungi may also be used in this invention. It is preferred to use plant promoters that do not cause expression of the polypeptide in bacteria.

Commonly used prokaryotic control sequences include promoters such as the beta lactamase (penicillinase) and lactose (lac) promoter systems (Chang et al., Nature 198: 1056 (1977)), the tryptophan (trp) promoter system (Goeddel et al., Nucleic Acids Res. 8:4057 (1980)) and the lambda derived P L promoter and N-gene ribosome binding site (Shimatake et al., Nature 292:128 (1981)). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Expression systems for expressing a protein of the present invention are available using *Bacillus* sp. and *Salmonella* (Palva et al., Gene 22:229–235 (1983); Mosbach et al., Nature 302:543–545 (1983)).

Synthesis of heterologous proteins in yeast is well known. See Sherman, F., et al., *Methods in Yeast Genetics*, Cold Spring Harbor Laboratory (1982). Two widely utilized yeast for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysates. The monitoring of the purification process can be accomplished by using Western blot techniques or radioimmunoassay of other standard immunoassay techniques.

The proteins of the present invention can also be constructed using non-cellular synthetic methods. Solid phase synthesis of proteins of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, Solid-Phase Peptide Synthesis, pp. 3–284 in *The Peptides: Analysis, Synthesis, Biology*. Vol. 2: *Special Methods in Peptide Synthesis*, Part A.; Merrifield et al., *J. Am. Chem. Soc*. 85: 2149–2156 (1963), and Stewart et al., *Solid Phase Peptide Synthesis,* 2nd ed., Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicycylohexylcarbodiimide) is known to those of skill.

The proteins of this invention may be purified to substantial purity by standard techniques well known in the art, including detergent solubilization, selective precipitation with such substances as ammonium sulfate, column chromatography, immunopurification methods, and others. See, for instance, R. Scopes, *Protein Purification: Principles and Practice*, Springer-Verlag: New York (1982); Deutscher, *Guide to Protein Purification*, Academic Press (1990). For example, antibodies may be raised to the proteins as described herein. Purification from *E. coli* can be achieved following procedures described in U.S. Pat. No. 4,511,503. Detection of the expressed protein is achieved by methods known in the art and include, for example, radioimmunoassays, Western blotting techniques or immunoprecipitation.

The present invention further provides a method for modulating (i.e., increasing or decreasing) the concentration or composition of the polypeptides of the present invention in a plant or part thereof. Modulation of the polypeptides can be effected by increasing or decreasing the concentration and/or the composition of the polypeptides in a plant. The method comprises transforming a plant cell with an expression cassette comprising a polynucleotide of the present invention to obtain a transformed plant cell, growing the transformed plant cell under plant forming conditions, and inducing expression of the polynucleotide in the plant for a time sufficient to modulate concentration and/or composition of the polypeptides in the plant or plant part.

In some embodiments, the content and/or composition of polypeptides of the present invention in a plant may be modulated by altering, in vivo or in vitro, the promoter of a non-isolated gene of the present invention to up- or downregulate gene expression. In some embodiments, the coding regions of native genes of the present invention can be altered via substitution, addition, insertion, or deletion. See, e.g., Kmiec, U.S. Pat. No. 5,565,350; Zarling et al., PCT/US93/03868.

In some embodiments, an isolated nucleic acid (e.g., a vector) comprising a promoter sequence is transfected into a plant cell. Subsequently, a plant cell comprising the isolated nucleic acid is selected for by means known to those of skill in the art such as, but not limited to, Southern blot, DNA sequencing, or PCR analysis using primers specific to the promoter and to the nucleic acid and detecting amplicons produced therefrom. A plant or plant part altered or modified by the foregoing embodiments is grown under plant forming conditions for a time sufficient to modulate the concentration and/or composition of polypeptides of the present invention in the plant. Plant forming conditions are well known in the art.

In general, concentration of the polypeptides is increased or decreased by at least 5%, 10%, 20%, 30%, 40%, 50%, 60%, 70%, 80%, or 90% relative to a native control plant, plant part, or cell lacking the aforementioned expression cassette. Modulation in the present invention may occur during and/or subsequent to growth of the plant to the desired stage of development.

Modulating nucleic acid expression temporally and/or in particular tissues can be controlled by employing the appropriate promoter operably linked to a polynucleotide of the present invention in, for example, sense or antisense orientation as discussed in greater detail above. Induction of expression of a polynucleotide of the present invention can also be controlled by exogenous administration of an effective amount of inducing compound. Inducible promoters and inducing compounds that activate expression from these promoters are well known in the art.

In preferred embodiments, the polypeptides of the present invention are modulated in monocots or dicots, preferably corn, soybean, sunflower, sorghum, canola, wheat, alfalfa, cotton, rice, barley, millet, and lupin.

Means of detecting the proteins of the present invention are not critical aspects of the present invention. In a preferred embodiment, the proteins are detected and/or quantified using any of a number of well recognized immunological binding assays (see, e.g., U.S. Pat. Nos. 4,366,241; 4,376,110; 4,517,288; and 4,837,168). For a review of the general immunoassays, see also Methods in Cell Biology, Vol. 37: *Antibodies in Cell Biology*, Asai, Ed., Academic Press, Inc. New York (1993); *Basic and Clinical Immunology* 7th Edition, Stites & Terr, Eds. (1991). Moreover, the immunoassays of the present invention can be performed in any of several configurations, e.g., those reviewed in *Enzyme Immunoassay*, Maggio, Ed., CRC Press, Boca Raton, Fla. (1980); Tijan, Practice and Theory of Enzyme Immunoassays, *Laboratory Techniques in Biochemistry and Molecular Biology*, Elsevier Science Publishers B.V., Amsterdam (1985); Harlow and Lane, supra; *Immunoassay: A Practical Guide*, Chan, Ed., Academic Press, Orlando, Fla. (1987); *Principles and Practice of Immunoassays*, Price and Newman Eds., Stockton Press, NY (1991); and *Non-isotopic Immunoassays*, Ngo, Ed., Plenum Press, NY (1988).

Typical methods for detecting proteins include Western blot (immunoblot) analysis, analytic biochemical methods such as electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like.

For a review of various labeling or signal producing systems which may be used, see, U.S. Pat. No. 4,391,904, which is incorporated herein by reference.

Some assay formats do not require the use of labeled components. For instance, agglutination assays can be used to detect the presence of the target antibodies.

The proteins of the present invention can be used for identifying compounds that bind to (e.g., substrates), and/or increase or decrease (i.e., modulate) the activity of, catalytically active polypeptides of the present invention. The method comprises contacting a polypeptide of the present invention with a compound whose ability to bind to or modulate activity is to be determined. Methods of measuring enzyme kinetics are well known in the art. See, e.g., Segel, *Biochemical Calculations*, $2^{nd}$ ed., John Wiley and Sons, New York (1976).

Antibodies can be raised to a protein of the present invention, including individual, allelic, strain, or species variants, and fragments thereof, both in their naturally occurring (full-length) forms and in recombinant forms. Additionally, antibodies are raised to these proteins in either their native configurations or in non-native configurations. Anti-idiotypic antibodies can also be generated. Many methods of making antibodies are known to persons of skill. Description of techniques for preparing such monoclonal antibodies are found in, e.g., *Basic and Clinical Immunology*, 4th ed., Stites et al., Eds., Lange Medical Publications, Los Altos, Calif., and references cited therein; Harlow and Lane, Supra; Goding, *Monoclonal Antibodies: Principles and Practice*, 2nd ed., Academic Press, New York, N.Y. (1986); and Kohler and Milstein, *Nature* 256:495–497 (1975).

Other suitable techniques involve selection of libraries of recombinant antibodies in phage or similar vectors (see, e.g., Huse et al., *Science* 246:1275–1281 (1989); and Ward et al., *Nature* 341:544–546 (1989); and Vaughan et al., *Nature Biotechnology*, 14: 309–314 (1996)). Alternatively, high avidity human monoclonal antibodies can be obtained from transgenic mice comprising fragments of the unrearranged human heavy and light chain lg loci (i.e., minilocus transgenic mice). Fishwild et al., *Nature Biotech.*, 14:845–851 (1996). Also, recombinant immunoglobulins may be produced. See, Cabilly, U.S. Pat. No. 4,816,567; and Queen et al., *Proc. Nat'l Acad. Sci.* 86:10029–10033 (1989).

The antibodies of this invention can be used for affinity chromatography in isolating proteins of the present invention, for screening expression libraries for particular expression products such as normal or abnormal protein or for raising anti-idiotypic antibodies which are useful for detecting or diagnosing various pathological conditions related to the presence of the respective antigens.

Frequently, the proteins and antibodies of the present invention will be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like.

Transfection/Transformation of Cells

The method of transformation/transfection is not critical to the invention; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method that provides for efficient transformation/transfection may be employed.

A DNA sequence coding for the desired polynucleotide of the present invention, for example a cDNA, RNA or a genomic sequence, will be used to construct an expression cassette that can be introduced into the desired plant. Isolated nucleic acid acids of the present invention can be introduced into plants according techniques known in the art. Generally, expression cassettes as described above and suitable for transformation of plant cells are prepared.

Techniques for transforming a wide variety of higher plant species are well known and described in the technical, scientific, and patent literature. See, for example, Weising et al., *Ann. Rev. Genet* 22:421–477 (1988). For example, the DNA construct may be introduced directly into the genomic DNA of the plant cell using techniques such as electroporation, PEG-mediated transfection, particle bombardment, silicon fiber delivery, or microinjection of plant cell protoplasts or embryogenic callus. See, e.g., Tomes et al., Direct DNA Transfer into Intact Plant Cells Via Microprojectile Bombardment. pp. 197–213 in Plant Cell, Tissue and Organ Culture, Fundamental Methods. eds. O. L. Gamborg and G. C. Phillips. Springer-Verlag Berlin Heidelberg New York, 1995. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616.

The introduction of DNA constructs using polyethylene glycol precipitation is described in Paszkowski et al., *Embo J.* 3:2717–2722 (1984). Electroporation techniques are described in Fromm et al., *Proc. Natl. Acad. Sci.* 82: 5824 (1985). Ballistic transformation techniques are described in Klein et al., *Nature* 327:70–73 (1987).

*Agrobacterium tumefaciens*-meditated transformation techniques are well described in the scientific literature. See, for example Horsch et al., *Science* 233:496–498 (1984), and Fraley et al., *Proc. Natl. Acad. Sci.* 80:4803 (1983). For instance, *Agrobacterium* transformation of maize is described in U.S. Pat. No. 5,550,318 and WO98/32326.

Other methods of transfection or transformation include (1) *Agrobacterium rhizogenes*-mediated transformation (see, e.g., Lichtenstein and Fuller In: Genetic Engineering, vol. 6, P W J Rigby, Ed., London, Academic Press, 1987; and Lichtenstein, C. P., and Draper, J,. In: DNA Cloning, Vol. II, D. M. Glover, Ed., Oxford, IRI Press, 1985), Application PCT/US87/02512 (WO 88/02405 published Apr. 7, 1988) describes the use of *A. rhizogenes* strain A4 and its Ri plasmid along with *A. tumefaciens* vectors pARC8 or pARC16 (2) liposome-mediated DNA uptake (see, e.g., Freeman et al., Plant Cell Physiol. 25:1353, 1984), (3) the vortexing method (see, e.g., Kindle, *Proc. Natl. Acad. Sci.*, USA 87:1228, (1990).

DNA can also be introduced into plants by direct DNA transfer into pollen as described by Zhou et al., Methods in Enzymology, 101:433 (1983); D. Hess, Intern Rev. Cytol., 107:367 (1987); Luo et al., Plane Mol. Biol. Reporter, 6:165 (1988). Expression of polypeptide coding nucleic acids can be obtained by injection of the DNA into reproductive organs of a plant as described by Pena et al., Nature, 325:274 (1987). DNA can also be injected directly into the cells of immature embryos and the rehydration of desiccated embryos as described by Neuhaus et al., Theor. Appl. Genet., 75:30 (1987); and Benbrook et al., in Proceedings Bio Expo 1986, Butterworth, Stoneham, Mass., pp. 27–54 (1986).

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art. Kuchler, R. J., *Biochemical Methods in Cell Culture and Virology*, Dowden, Hutchinson and Ross, Inc. (1977).

Transgenic Plant Regeneration

Transformed plant cells which are derived by any of the above transformation techniques can be cultured to regenerate a whole plant which possesses the transformed genotype. Such regeneration techniques often rely on manipulation of certain phytohormones in a tissue culture growth medium, typically relying on a biocide and/or herbicide marker which has been introduced together with a polynucleotide of the present invention. For transformation and regeneration of maize see, Gordon-Kamm et al., The Plant Cell, 2:603–618 (1990).

Plants cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., *Protoplasts Isolation and Culture, Handbook of Plant Cell Culture*, Macmillan Publishing Company, New York, pp. 124–176 (1983); and Binding, *Regeneration of Plants, Plant Protoplasts*, CRC Press, Boca Raton, pp. 21–73 (1985).

The regeneration of plants containing the foreign gene introduced by *Agrobacterium* can be achieved as described by Horsch et al., *Science*, 227:1229–1231 (1985) and Fraley et al., *Proc. Natl. Acad. Sci. U.S.A.*, 80:4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof. Such regeneration techniques are described generally in Klee et al., *Ann. Rev. of Plant Phys.* 38:467–486 (1987). The regeneration of plants from either single plant protoplasts or various explants is well known in the art. See, for example, Methods for Plant Molecular Biology, A. Weissbach and H. Weissbach, eds., Academic Press, Inc., San Diego, Calif. (1988). For maize cell culture and regeneration see generally, *The Maize Handbook*, Freeling and Walbot, Eds., Springer, N.Y. (1994); *Corn and Corn Improvement*, 3rd edition, Sprague and Dudley Eds., American Society of Agronomy, Madison, Wis. (1988).

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, stems, stalks, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing a selectable marker can be screened for transmission of the nucleic acid of the present invention by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Back-crossing to a parental plant and out-crossing with a non-transgenic plant are also contemplated.

Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., *Plant Molecular Biology: A Laboratory Manual*, Chapter 7, Clark, Ed., Springer-Verlag, Berlin (1997). For molecular marker methods, see generally, The DNA Revolution by Andrew H. Paterson 1996 (Chapter 2) in: Genome Mapping in Plants (ed. Andrew H. Paterson) by Academic Press/R. G. Landis Company, Austin, Tex., pp. 7–21.

The particular method of genotyping in the present invention may employ any number of molecular marker analytic techniques such as, but not limited to, restriction fragment length polymorphisms (RFLPs). RFLPs are the product of allelic differences between DNA restriction fragments caused by nucleotide sequence variability. Thus, the present invention further provides a means to follow segregation of a gene or nucleic acid of the present invention as well as chromosomal sequences genetically linked to these genes or nucleic acids using such techniques as RFLP analysis.

Plants that can be used in the method of the invention include monocotyledonous and dicotyledonous plants. Preferred plants include corn, soybean, sunflower, sorghum, canola, wheat, alfalfa, cotton, rice, barley, lupin and millet.

Seeds derived from plants regenerated from transformed plant cells, plant parts or plant tissues, or progeny derived from the regenerated transformed plants, may be used directly as feed or food, or further processing may occur.

Antibodies

The proteins encoded by polynucleotides of this embodiment, when presented as an immunogen, elicit the production of polyclonal antibodies which specifically bind to a prototype protease inhibitor polypeptide such as, but not limited to, a polypeptide encoded by the polynucleotide of (b), supra, or exemplary polypeptides of SEQ ID NOS: 6, 8, 10, 12, 14, 16, 18 and 20. Generally, however, a protein encoded by a polynucleotide of this embodiment does not bind to antisera raised against the prototype protease inhibitor polypeptide when the antisera has been fully immunosorbed with the reference protease inhibitor polypeptide. Methods of making and assaying for antibody binding specificity/affinity are well known in the art. Exemplary immunoassay formats include ELISA, competitive immunoassays, radioimmunoassays, Western blots, indirect immunofluorescent assays and the like.

In a preferred assay method fully immunosorbed and pooled antisera which is elicited to the prototype polypeptide can be used in a competitive binding assay to test the protein. The concentration of the prototype polypeptide required to inhibit 50% of the binding of the antisera to the prototype polypeptide is determined. If the amount of the protein required to inhibit binding is less than twice the amount of the prototype protein, then the protein is said to specifically bind to the antisera elicited to the immunogen. Accordingly, the proteins embrace allelic variants, conservatively modified variants, and minor recombinant modifications to a prototype protease inhibitor polypeptide.

CI-2 Engineering

Numbering of amino acid positions refers to the full length wild-type CI-2 (SEQ I.D. NO. 2) unless stated otherwise. Wild type CI-2 (from barley) contains 8 lysines, one methionine, four threonines, and one tryptophan (SEQ I.D. NO. 2). A truncated form of wild type CI-2 used in the present study (SEQ I.D. NO. 4) comprises residues 19 through 83 of the full-length wild-type plus a start methionine. Using methods known in the art for genetic and protein engineering, barley high lysine (BHL) variants with increased levels of essential amino acids were made. Preferred barley & maize variants will have increased levels of lysine, threonine, tryptophan or methionine, or combinations thereof.

BHL1 (SEQ I.D. NO. 6) contains 14 lysines. BHL2 (SEQ I.D. NO. 8) and BHL3 (SEQ. I.D. NO. 10) each contain 15 lysines. BHL1 has lysine substitutions at wild-type (SEQ I.D. NO. 2) positions 19, 34, 41, 56, 59, 62, 67, and 73 (BHL1 positions 2, 17, 24, 39, 42, 45, 50 and 56). BHL2 contains these same substitutions plus a lysine at wild-type (SEQ I.D. NO. 2) position 65 (BHL2 position 48). BHL2 also contains alanine substitutions for wild-type residues threonine-58 and glutamate-60 (threonine-41 and glutamate43 of BHL2). The BHL3 sequence is identical to BHL2 except that these two residues at wild type positions 58 and 60 were substituted with glycine and histidine, respectively, rather than with alanine. BHL3N (SEQ. I.D. NO. 12) contains the same substitutions as BHL3, plus four lysine substitutions in the 18 additional amino acid residues in the amino terminal region, for a total of 20 lysines. The BHL4 sequence (SEQ I.D. NO. 14) is the same as BHL1 except that the residue at wild type position 59 (BHL4 position 42) is glycine, rather than lysine. BHL5, BHL6, and BHL8 were designed to have an increased content of methionine, threonine, and tryptophan, as well as lysine. BHL5 (SEQ I.D. NO. 16) contains lysine substitutions at wild type positions 19, 34, 41, 47, 56, 62, 67, 73, 75, 78, and 81 (BHL5 positions 3, 18, 25, 31, 40, 46, 51, 57, 59, 62, and 65). BHL5 also contains methonine substitutions at wild-type positions 17 (start methionine for BHL5), 20, 38, 40, 49, and 63, corresponding to BHL5 positions 1, 4, 22, 24, 33, and 47. BHL5 also contains tryptophan substitutions at wild-type positions 61 and 69 (BHL5 positions 45 and 53), as well as threonine substitutions at wild-type positions 23, 31, and 79 (BHL5 positions 7, 15, and 63). BHL5 contains 17 lysines, six methionines, three tryptophans, and six threonines. BHL5 also contains the glycine substitution at wild-type position 59 (BHL5 position 43). BHL6 (SEQ. I.D. NO. 18) has the same sequence as that of BHL5, except that the residue at wild-type position 67 (BHL6 position 49) is arginine, rather than lysine. BHL8 (SEQ. I.D. NO. 20) has the same sequence as BHL6 except that cysteines were substituted at wild-type positions 22 and 82 (BHL8 positions 6 and 66).

The active site loop region encompasses an extended loop region from about amino acid residue 53 to about amino acid residue 70. Destabilization of the reactive loop was achieved by substituting the non-wild type amino acids residues at about positions 53 to about 70. Preferably, the following mutations are made (all numbering corresponds to SEQ. I.D. NO. 2 unless otherwise stated): Arg62→Lys62, Arg65→Lys65, Arg67→Lys67, Thr58→Ala58 or Gly58, and Glu60→Ala60 or His60. As an alternative approach to decreasing inhibitory activity without substantial destabilization of the active site loop, methionine 59 was changed to glycine. A glycine at this position is not known in any naturally occurring CI-2 homologs.

The first 18 residues in the wild type CI-2 do not assume any ordered conformation and also do not contribute to the structural integrity of the molecule (see e.g. Kjaer, et al., Carlsberg Res. Commun.; Vol. 53; pp. 327–354; (1987);

incorporated herein in its entirety by reference), a full length 83 residue version was created in which residues one or more 1,8,11, and 17 were also replaced with one or more non-native amino acids. In one embodiment residues 1,8,11, and 17 were cysteine and conservative substitutions. In a preferred embodiment the non-native residues are methionine and lysine replaced with essential amino acids. The resulting compound has the sequence indicated in SEQ ID No. 12. Additionally, substitution of residues threonine, at position 58, and glutamic acid, at position 60, with glycine and histidine, respectively, resulted in a protein with lowered protease inhibitor activity. The resulting compound has the sequence indicated in Sequence I.D. No. 5. The full length engineered CI-2 containing 21 lysine residues (25.3%) has also been expressed in and purified from E. coli.

In one embodiment, the CI-2-like protein has elevated essential amino acid content. Optionally, the CI-2-like protein has both elevated essential amino acid content and reduced protease inhibitor activity.

Criteria in determining sequences with homology to the present invention include determination of homology through sequence alignment using amino acids 24W, 35A, and 66V, for example and/or the amino acids 24–29, 54–58, 65–71 and/or 80–83. Alignment of these conserved residues provide a method for aligning sequences and corresponding them and their residue numbers to Seq. I.D. No. 2. Once aligned, native amino acid residues can be substituted with essential amino acids at the same residues identified as substitutable in Seq. ID No. 2.

These polypeptide comprise substituted CI-2-like polypeptides, or truncated versions thereof substituted to contain 7 or more non-native essential amino acid residues at positions corresponding to positions in Sequence ID. No.2 selected from residues 1, 8, 11, 17, 18, 19, 20, 22, 23, 31, 34, 38, 40, 41, 47, 49, 56, 58, 59, 60, 61, 62, 63, 65, 67, 69, 73, 75, 76, 78, 79, 81, 82, or combinations thereof. In another embodiment the substituted CI-2-like protein has addition non-native residues at positions 32, 45, 53, 64, 70, 74, and 77. In one embodiment the substituted CI-2-like protein has 7 or more substitutions. In another embodiment the substituted CI-2-like protein has more than 8 or more than 9 substitutions. In still another embodiment the substituted CI-2-like protein has more than 10 or more than 11. In still another embodiment the substituted CI-2-like protein has more than 14 or more than 16. In still another embodiment the substituted CI-2-like protein has more than 20 or more than 25. In still another embodiment the substituted CI-2-like protein has more than 27 or more than 30. In still another embodiment the substituted CI-2-like protein has more than 32 or more than 34. In still another embodiment the substituted CI-2-like protein has more than 35 or more than 40. In still another embodiment the substituted CI-2-like protein has more than 42 or more than 45.

In another embodiment this invention comprises a substituted CI-2-like protein with an non-native essential amino acid residue in more than about 11% to less than about 75% of the amino acid residues.

For example these CI-2-like polypeptides could be substituted to contain, G19K, I38M, or R41K in accordance with the present invention. These modifications can be made using methods known in the art with the material and methods described in the instant specification.

Genes that have the desired effect are selected using procedures described in the instant specification.

In one embodiment the substituted CI-2-like protein has a non-native essential amino acid in more than about 11% to less than about 80% of the amino acid residues. In another embodiment a non-native essential amino acid residue is in more than about 12% to less than about 75% of the amino acid residues. In another embodiment a non-native essential amino acid residue is in more than about 15% to less than about 75% of the amino acid residues. In another embodiment a non-native essential amino acid residue is in more than about 15% to less than 70%. In another embodiment a non-native essential amino acid residue is in more than about 20% to less than 70%. In another embodiment a non-native essential amino acid residue is in more than about 25% to less than 65%. In another embodiment a non-native essential amino acid residue is in more than about 30% to less than 60%. In another embodiment a non-native essential amino acid residue is in more than about 50% to less than about 80% of the amino acid residues.

A substituted CI-2-like polypeptide may have from about 55 to about 90% total essential amino acid content. In one embodiment the substituted CI-2-like polypeptide has from about 60 to about 90% total essential amino acid content. In another embodiment the substituted CI-2-like polypeptide has from about 60 to about 85% total essential amino acid content. In another embodiment the substituted CI-2-like polypeptide has from about 70 to about 90% total essential amino acid content. In another embodiment the substituted CI-2-like polypeptide has 75–90% total essential amino acid content.

In one embodiment the substituted CI-2-like protein may have other modifications. In one embodiment the substituted protein has a free energy of unfolding of more than about 3.5 to about 15 Kcal/mol. In another embodiment the free energy of unfolding is more than about 4 to about 10 Kcal/mol. In another embodiment the free energy of unfolding is more than about 6 to about 10 Kcal/mol.

The substituted CI-2-like protein is made more stable by the addition of disulfide bonds. In one embodiment from one to less than 5 disulfide bonds are added. In another embodiment from one to less than 3 disulfide bonds are added. In another embodiment one disulfide bond is added. In one embodiment the disulfide bonds comprise residues [E23C and R81C] or [T22C and V82C] or [V53C and V70C]. In a preferred embodiment the disulfide bond comprises residues T22C and V82C. In another preferred embodiment the disulfide bond comprises residues E23C and R81C.

The present invention also includes the substituted CI-2-like protein with an amino terminal extension. In one embodiment the extension is for nutritional enhancement. In another embodiment the extension is a start signal, a transit sequence, a transit peptide, a signal peptide, a fusion protein, a cleavable peptide, a CI-2-like polypeptide or an uncleaved peptide. In one embodiment the CI-2 polypeptide has at least 1 to about 18 residues. In another embodiment the extension contains a nutritionally-enhancing polypeptide. In another embodiment the nutritionally-enhancing polypeptide contains essential amino acids.

The substituted CI-2-like protein with essential amino acid substitutions may also have a modified protease activity. In one embodiment the protease activity is changed in specificity.

In one embodiment of the present invention, the substituted CI-2-like protein is digestible. In one embodiment the protein is digested in simulated gastric fluid. In another embodiment the protein is digested in simulated intestinal fluid.

In one embodiment of the present invention, truncated versions include any consecutive 23 amino acids. In another embodiment the truncated version excludes the region corresponding to the amino terminal 17 or 18 amino acids of SEQ ID NO. 2. In another embodiment, substitutions are at 7 or more residues. In another embodiment the substituted CI-2-like protein has more than 8 or more than 9 substitutions. In still another embodiment the substituted CI-2-like protein has more than 10 or more than 11. In still another embodiment the substituted CI-2-like protein has more than 14 or more than 16. In still another embodiment the substituted CI-2-like protein has more than 20 or more than 25. In still another embodiment the substituted CI-2-like protein has more than 27 or more than 30. In still another embodiment the substituted CI-2-like protein has more than 32 or more than 34. In still another embodiment the substituted CI-2-like protein has more than 35 or more than 40. In still another embodiment the substituted CI-2-like protein has more than 42 or more than 45.

In one embodiment the substituted CI-2-like protein exhibits reduced inhibiting activity against chymotrypsin, subtilisin and elastase. In another embodiment the substituted CI-2-like protein exhibits no inhibitory activity against chymotrypsin and elastase.

In one embodiment the substituted CI-2-like protein has 2 or more or 3 or more substitutions. In another embodiment the substituted CI-2-like protein has more than 4 or more than 5 substitutions. In still another embodiment the substituted CI-2-like protein has more than 7 or more than 9. In still another embodiment the substituted CI-2-like protein has more than 10 or more than 11. In still another embodiment the substituted CI-2-like protein has more than 12 or more than 15. In still another embodiment the substituted CI-2-like protein has more than 17 or more than 20. In still another embodiment the substituted CI-2-like protein has more than 22 or more than 24. In still another embodiment the substituted CI-2-like protein has more than 25 or more than 27. In still another embodiment the substituted CI-2-like protein has more than 30 or more than 35.

In one embodiment an essential amino acid is methionine, threonine, lysine, isoleucine, leucine, valine, tryptophan, phenylalanine, and histidine. In another embodiment the essential amino acid is lysine, threonine, tryptophan, methionine, or combinations and conservative substitutions thereof.

The following conservative essential amino acid substitutions are included in the present invention: [M, I, L, V] or [K, T]. K is replaceable with T. M, I, L and V are replaceable with each other.

For example selection of [E34K] and [I56M, T58G, M59G, E60H, Y61W, R62K] provides substituted CI-2-like polypeptide having the residues of SEQ ID NO. 2 at all positions except 34, 56, 58, 59, 60, 61 and 62 where amino acids are K, M, G, G, H, W, & K, respectively.

Nutritional enhancement may also be provided through insertion into the active site loop region. In one embodiment this insert is one or more of a combination of essential amino acids.

In a preferred embodiment the insert is a peptide of from 2 to 20 amino acids. In another embodiment the peptide is from 5 to 15 amino acids. In another embodiment the essential amino acids are lysine, threonine, methionine or tryptophan or combinations thereof.

One embodiment of the present invention provides an isolated polypeptide comprising a plant substituted CI-2-like polypeptide having the following composition: 15–35 mole % lysine, 5–15 mole % methionine, 6–25 mole % threonine, 4–9 mole % tryptophan or combinations thereof. In another embodiment the plant substituted CI-2-like polypeptide has the following composition: 20–35 mole % lysine, 7–15 mole % methionine, 10–25 mole % threonine, 6–9 mole % tryptophan or combinations thereof.

In one embodiment the substituted CI-2-like polypeptide is proteolytically stable, as demonstrated by detection of the intact polypeptide based upon detection on SDS-PAGE gel, following a 30 minute incubation at 37° C. in 100 mM Tris-HCl, 50 mMNaCl, 1 mMCaCl$_2$, pH 8, with a 10:1 (weight to weight ratio) of polypeptide:protease, with the protease being either chymotrypsin or trypsin.

In one embodiment of the present invention an isolated polypeptide comprises at least 23 contiguous amino acids with more than 79% sequence identity, to the polypeptide of Seq. ID No. 20, wherein the % sequence identity is based on the 23 contiguous amino acids sequence and is determined by GAP analysis using Gap Weight of 8 and Length Weight of 2. In another embodiment an isolated polypeptide comprises at least 23 contiguous amino acids with more than 81% sequence identity, to the polypeptide of Seq. ID No. 20. In another embodiment an isolated polypeptide comprises at least 23 contiguous amino acids with more than 83% sequence identity, to the polypeptide of Seq. ID No. 20. In another embodiment an isolated polypeptide comprises at least 23 contiguous amino acids with more than 85% sequence identity, to the polypeptide of Seq. ID No. 20. In another embodiment an isolated polypeptide comprises at least 23 contiguous amino acids with more than 89% sequence identity, to the polypeptide of Seq. ID No. 20.

In one embodiment of the present invention, the polynucleotide has at least 73% sequence identity to SEQ ID NO: 19, wherein the % sequence identity is based on the entire sequence and is determined by BLAST 2.0. In another embodiment the polynucleotide has at least 75% or 77% sequence identity to SEQ ID NO: 19. In another embodiment the polynucleotide has at least 80% or 85% sequence identity to SEQ ID NO: 19. In another embodiment the polynucleotide has at least 90% or 95% sequence identity to SEQ ID NO: 19. In another embodiment the polynucleotide has 98 sequence identity to SEQ ID NO: 19.

In an embodiment of the present invention, the polynucleotide comprising at least 25 nucleotides in length which hybridizes under low stringency conditions to a polynucleotide having the sequence set forth in SEQ ID NOs: 19, wherein the conditions include hybridization with a buffer solution of 30% formamide, 1M NaCl, 1% SDS at 37° C. for 24 hours and a wash in 2×SSC at 50° C., 3× for 15 minutes.

Modification in the active site loop area by amino acid substitution or other means, destroys the hydrogen bonding and changes or reduces the protease inhibitor activity of BHL. Substitution of amino acid residues threonine, at position 58, and glutamic acid, at position 60, with glycine and histidine, respectively, resulted in a protein with lowered protease inhibitor activity. Residue 59, when changed, is able to modifying protease inhibitor activity and change specificity. When this residue was changed to a lysine, the protease inhibition specificity was changed from a chymotrypin inhibitor to a trypsin inhibitor. When residue 59 was changed to glycine, the inhibitory activity against trypsin was removed, and inhibitory activity against chymotrypsin, subtilisin, and elastase was considerably reduced compared to wild type CI-2.

Proteins

Synthesis of the compounds is performed according to methods of peptide synthesis which are well known in the art and thus constitute no part of this invention. For example, in vitro, the compounds can be synthesized on an applied Biosystems model 431a peptide synthesizer using fast-moc™ chemistry involving hbtu [2-(lh-benzotriazol-1-yl)-1,1,3,3-tetramethyluronium hexafluorophosphate, as published by Rao, et al., Int. J. Pep. Prot. Res.; Vol. 40; pp. 508–515; (1992); incorporated herein in its entirety by reference. Peptides can be cleaved following standard protocols and purified by reverse phase chromatography using standard methods. The amino acid sequence of each peptide can be confirmed by automated edman degradation on an applied biosystems 477a protein sequencer/120a pth analyzer. More preferably, however, the compounds of this invention are synthesized in vivo by bacterial or plant cells which have been transformed by insertion of an expression cassette containing a synthetic gene which when transcribed and translated yields the desired compound. Such empty expression cassettes, providing appropriate regulatory sequences for plant or bacterial expression of the desired sequence, are also well-known, and the nucleotide sequence for the synthetic gene, either RNA or DNA, can readily be derived from the amino acid sequence for the protein using standard reference texts. Preferably, such synthetic genes will employ plant-preferred codons to enhance expression of the desired protein.

Promoters that may be used in the genetic sequence include NOS, OCS and CaMV promoters.

This invention provides a method for increasing essential amino acid levels in *Agrobacterium tumefaciens*-susceptible dicotyledonous plants in which the expression cassette is introduced into the cells by infecting the cells with *Agrobacterium tumefaciens*, a plasmid of which has been modified to include a plant expression cassette of this invention. *Agrobacterium tumefaciens*-mediated transformation is also effective for monocotyledonous plants.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Variations on the above embodiments are within the ability of one of ordinary skill in the art, and such variations do not depart from the scope of the present invention as described in the following claims.

The present invention will be further described by reference to the following detailed examples. It is understood, however, that there are many extensions, variations, and modifications on the basic theme of the present invention beyond that shown in the examples and description, which are within the spirit and scope of the present invention. All publications, patents, and patent applications cited herein are hereby incorporated by reference.

Assays for Compounds that Modulate Protease Inhibitory Activity or Expression

The present invention also provides means for identifying compounds that bind to (e.g., substrates), and/or increase or decrease (i.e., modulate) the inhibitory activity of, protease inhibitor polypeptides. The method comprises contacting a protease inhibitor polypeptide of the present invention with a compound whose ability to bind to or modulate inhibitory activity is to be determined. The protease inhibitor polypeptide employed will have at least 20%, preferably at least 30% or 40%, more preferably at least 50% or 60%, and most preferably at least 70% or 80% of the inhibitory activity of the full-length (native and endogenous) protease inhibitor polypeptide. Generally, the protease inhibitor polypeptide will be present in a range sufficient to determine the effect of the compound, typically about 1 nM to 10 μM. Likewise, the compound will be present in a concentration of from about 1 nM to 10 μM. Those of skill will understand that such factors as enzyme concentration, ligand concentrations (i.e., substrates, products, inhibitors, activators), pH, ionic strength, and temperature will be controlled so as to obtain useful kinetic data and determine the presence of absence of a compound that binds or modulates protease inhibitor polypeptide activity. Methods of measuring enzyme kinetics is well known in the art. See, e.g., Segel, *Biochemical Calculations*, $2^{nd}$ ed., John Wiley and Sons, New York (1976).

Although the present invention has been described in some detail by way of illustration and example for purposes of clarity of understanding, it will be obvious that certain changes and modifications may be practiced within the scope of the appended claims.

EXAMPLES

Example 1

Construction of Expression Cassettes

Vector construction was based upon the published WT CI-2A sequence information Williamson et al, Eur. J. Biochem 165:99–106 (1987) and SEQ ID NO 1. Methods for obtaining full length or truncated wild-type CI-2 DNA include, but are not limited to PCR amplification, from a barley (or other plant) endosperm cDNA library using oligonucleotides derived from Seq. ID No 1 or from the published sequence supra, using probes derived from the same on a barley endosperm cDNA library, or using a set of overlapping oligonucleotides that encompass the gene, or having the gene synthesized by a commercial vendor such as The Midland Certified Regeant Company (Midland, Tex.).

BHL1

The BHL1 insert corresponds to SEQ ID NO 5. Oligonucleotide pairs, N4394/N4395, and N4396/N4397, were annealed and ligated together to make a 202 base pair double stranded DNA molecule with overhangs compatible with Rca I and Nhe I restriction sites. PCR was performed on the annealed molecule using primers N5045 and N5046 to add a 5' Spe I site and 3' Hind III site. The PCR product was then restriction digested at those sites and ligated into pBluescript II KS+ at Spe I and Hind III sites. The insert was then removed by restriction digestion with Rca I and Hind III and was ligated into the Nco I and Hind III sites of pET28a (Novagen) to form the BHL1 construct.

```
Oligonucleotide sequences (5' to 3'):
N4394
  1    CATGAAGCTG AAGACAGAGT GGCCGGAGTT GGTGGGGAAA

TCGGTGGAGA

51    AAGCCAAGAA GGTGATCCTG AAGGACAAGC CAGAGGCGCA

AATCATAGTT

101    CTGC

N4395
  1    CAACCGGCAG AACTATGATT TGCGCCTCTG GCTTGTCCTT

CAGGATCACC

51    TTCTTGGCTT TCTCCACCGA TTTCCCCACC AACTCCGGCC

ACTCTGTCTT

101    CAGCTT

N4396
  1    CGGTTGGTAC AAAGGTGACG AAGGAATATA AGATCGACCG

CGTCAAGCTC

51    TTTGTGGATA AAAAGGACAA CATCGCGCAG GTCCCCAGGG

TCGG
```

```
N4397
1     CTAGCCGACC CTGGGGACCT GCGCGATGTT GTCCTTTTTA

TCCACAAAGA

51    GCTTGACGCG GTCGATCTTA TATTCCTTCG TCACCTTTGT

AC

N5045
1     GTACTAGTCA TGAAGCTGAA GACAGA

N5046
1     GAGAAGCTTG CTAGCCGACC CTGGGAC
```

BHL2

The BHL2 construct insert corresponds to SEQ ID NO 7. An overlap PCR strategy was used to make the BHL2 construct. PWO polymerase from Boehringer-Mannheim was used for all PCR reactions. The primers were chosen to change 3 amino acids in the BHL1 active site loop region, and to create unique Age I and Hind III restriction sites flanking the active site loop, to facilitate loop replacement in future constructs. A unique Rca I site (compatible with Nco I) was included at the 5' end, and a unique Xho I site was included at the 3' end. The overlap PCR was done as follows: PCR was done with primers N13561 and N13564, using the BHL1 construct as template. A separate PCR was done with primers N13563 and N13562, again using the BHL1 construct as template. The products from both reactions were gel purified and combined. Primer N13565, which overlapped regions on both of the PCR products, was then added and another PCR was done to generate the full-length insert. The resulting product was amplified by another PCR with primers N13561 and N13562. It was subsequently suspected that a deletion was present in N13562 that caused a frameshift near the 3' end of the PCR product. To avoid this frameshift problem, a final PCR reaction was done with primers N13562 and N13905. The final PCR product was digested with Rca I and Xho I, and then ligated into the Nco I and Xho I sites of pET 28b. Note: Some primers had 6-oligonucleotide extensions to improve restriction digestion efficiency.

```
Oligonucleotide sequences (5' TO 3'):
N13561
1     TTTTTTTCATGAAGCTGAAGACA

N13562
(as
ordered)
1     TTTTTTCTCGAGGCTAGCCGACCCTGGGGA

N13563
1     ATCGACAAGGTCAAGCTTTTTGTGGATAAAAAGGA

N13564
1     CACCTTTGTACCAACCGGTAGAACTATGATTTGCGC

N13565
1     GTTGGTACAAAGGTGGCGAAGGCCTATAAGATCGACAAGGTCAA

G

N13905
1     TTTTTTCTCGAGGCTAGCCGACCCTGGGGACCTGCGCTA
```

BHL3

The BHL3 construct insert corresponds to SEQ ID NO 9. The BHL2 construct was digested with Age I and Hind III, and the region between these sites was removed by gel purification and discarded. Oligonucleotide pairs, N14471 and N14472, were annealed to make a double stranded DNA molecule with overhangs compatible with Age I and Hind III restriction sites. The annealed product was ligated into the Age I and Hind III sites of the digested BHL2 construct to yield the BHL3 construct.

```
Oligonucleotide sequences (5' to 3'):
N14471
1     CCGGTTGGTACAAAGGTGGGTAAGCATTATAAGATCGACAAGGT

CA

N14472
1     AGCTTGACCTTGTCGATCTTATAATGCTTACCCACCTTTGTACC

AA
```

BHL3N

The BHL3N construct insert corresponds to SEQ ID No 11. A PCR reaction was done with the BHL3 construct as template. The primers for this reaction were N13771 and N13905. The resulting PCR product was digested with Rca I and Xho I and ligated into the Nco I and Xho I sites of pET 28b to yield the BHL3N construct.

```
Oligonucleotide sequences (5' to 3'):
N13771
1     TTTTTTTCATGAAGTCGGTGGAGAAGAAACCGAAGGGTGTGAAG

ACAGGTGCGGGTGACAAGCATAAGCTGAAGACAGAGTG

N13905 (already provided in BHL2 description).
```

BHL4

The BHL4 construct insert DNA corresponds to SEQ ID NO 13. The BHL2 construct was digested with Age I and Hind III, and the region between these sites was removed by gel purification and discarded. Oligonucleotide pairs, N22098 and N22099, were annealed to make a double stranded DNA molecule with overhangs compatible with Age I and Hind III restriction sites. The annealed product was ligated into the Age I and Hind III sites of the digested BHL2 construct to yield the BHL4 construct.

```
Oligonucleotide sequences (5' to 3'):
N22098
1     CCGGTTGGTACAAAGGTGACGGGCGAATACAAGATCGACCGCGT

CA

N22099
1     AGCTTGACGCGGTCGATCTTGTATTCGCCCGTCACCTTTGTACC

AA
```

BHL5

The BHL5 construct insert DNA corresponds to SEQ ID NO 15. This gene was synthesized by a commercial vendor, The Midland Certified Reagent Company (Midland, Tex.). The gene was supplied by Midland following digestion by Nco I and Hind III, and was ligated into the Nco I and Hind III sites of pET 28b to yield the BHL5 construct.

BHL6

The BHL6 construct insert DNA corresponds to SEQ ID NO 17. The BHL5 construct was digested with Age I and Sal I, and the region between these sites was removed by gel purification and discarded. Oligonucleotide pairs, N23923 and N23924, were annealed to make a double stranded DNA molecule with overhangs compatible with Age I and Sal I restriction sites. The annealed product was ligated into the Age I and Sal I sites of the digested BHL5 construct to yield the BHL6 construct.

```
Oligonucleotide sequences (5' to 3'):
  N23923
  1         CCGGTGAATGGAAGATGGATCGCGTCCGCCTCTGGG

N23924
  1         TCGACCCAGAGGCGGACGCGATCCATCTTCCATTCA
```

BHL8

The BHL8 construct insert DNA corresponds to SEQ ID No 19. A PCR reaction was done using the BHL6 construct as template. The primers for this reaction were N26671 and N26672. The resulting PCR product was digested with Nco I and Hind III and ligated into the Nco I and Hind III sites of pET 28b to yield the BHL8 construct.

```
Oligonucleotide sequences (5' to 3'):
N26671
1     TTTTTTCCATGGCTAAGATGAAGTGCACGTGGCCTGAGCTGGT

N26672
1     TTTTTTAAGCTTGGATCCCTAGCCGCACTTCGGAGTCTTGGCGA
```

The following experiments used truncated wild type CI-2.

Example 2

Expression of BHL Proteins in *E. coli*. Purification, and Verification of Recombinant Protein Sequence Expression in *E. coli*

BHL1, BHL2, BHL3, BHL3N, BHL4, BHL5, BHL6, BHL8, and the truncated wild-type CI-2 were expressed in *E. coli* using materials and methods from Novagen, Inc. The Novagen expression vector pET-28 was used (pET-28a for WT CI-2 and BHL1, and pET-28b for the other proteins). *E. coli* strains BL21(DE-3) or BL21(DE-3)pLysS were used. Cultures were typically grown until an OD at 600 nm of 0.8 to 1.0, and then induced with 1 mM IPTG and grown another 2.5 to 5 hours before harvesting. Induction at an OD as low as 0.4 was also done successfully. Growth temperatures of 37 degrees centigrade and 30 degrees centigrade were both used successfully. The media used was 2xYT plus the appropriate antibiotic at the concentration recommended in the Novagen manual.

Purification a. WT CI-2 (truncated)—Lysis buffer was 50 mM Tris-HCl, pH 8.0, 1 mM EDTA, 150 mM NaCl. The protein was precipitated with 70% ammonium sulfate. The pellet was dissolved and dialyzed against 50 mM Tris-HCl, pH 8.6. The protein was loaded onto a Hi-Trap Q column, and the unbound fraction was collected and precipitated in 70% ammonium sulfate. The pellet was dissolved in 50 mM sodium phosphate, pH 7.0, 200 mM NaCl, and fractionated on a Superdex-75 26/60 gel filtration column. Fractions were pooled and concentrated.

b. BHL1—Lysis buffer was 50 mM sodium phosphate, pH 7.0, 1 mM EDTA. The protein was loaded onto an SP Sepharose FF 16/10 column, washed with 150 mM NaCl in 50 mM sodium phosphate, pH 7.0, and then eluted with an NaCl gradient in 50 mM sodium phosphate. BHL1 eluted at approximately 200 mM NaCl. Fractions were pooled and concentrated.

c. BHL2, BHL3, BHL3N, BHL4, BHL5, BHL6, and BHL8—Lysis buffer was 50 mM Hepes, pH 8.0, 2 mM EDTA, 0.1% Triton X-100, and 0.5 mg/ml lysozyme. The protein was loaded onto an SP-Sepharose cation exchange column (typically a 5 to 10 ml size), washed with 50 mM sodium phosphate, pH 7.0, and step eluted with increasing concentrations of NaCl in 50 mM sodium phosphate, pH 7.0. The protein was concentrated and then subjected to Superdex-75 gel filtration chromatography. The Superdex chromatography was done in 50 mM Tris-HCl, 150 mM NaCl, pH 8.6 for BHL8, and in 50 mM sodium phosphate, 150 mM NaCl, pH 7.0 for the other proteins.

Storage

The purified proteins were stored long term by freezing in liquid nitrogen and keeping frozen at −70 degrees centigrade.

Verifcation of Recombinant Protein Sequence a. DNA sequencing—The insert region of these pET 28 constructs was confirmed by DNA sequencing.

b. N-terminal protein sequencing—100 µg of purified BHL3 were digested with 1 µg of chymotrypsin (Sigma catalog # C-4129) for 30 min at 37 degrees centigrade in 50 mM sodium phosphate, pH 7.0. The resulting chymotryptic fragments were purified by reversed phase chromatography, using an acetonitrile gradient for elution. Three pure peaks were observed and were sent to the University of Michigan Medical School Protein Structure Facility for N-terminal sequencing (6 cycles). Peak 1 had an N-terminal sequence of val-asp-lys-lys-asp-asn. Peak 2 had an N-terminal sequence of lys-ile-asp-lys-val-lys. Peak 3 had an N-terminal sequence of met-lys-leu-lys-thr-glu. These results demonstrate that chymotrypsin cleaved BHL3 after tyr-61 and phe-69. The N-terminal sequences all match exactly the BHL3 expected sequence, assuming that the start methionine was largely retained in the recombinant protein. This experiment verifies that the protein we expressed in and purified from *E. coli* was BHL3.

160 µg of BHL3N were digested with 1.6 µg pepsin overnight, and the resulting peptic fragments were purified by reversed phase chromatography. Five of the resulting peaks were sent to the Iowa State University Protein Facility for N-terminal sequencing through four cycles. The N-terminal sequences of the 5 peaks were: val-gly-lys-ser, phe-val-asp-lys, pro-val-gly-thr, met-lys-ser-val, and ile-ile-val-leu, all of which exactly match the expected BHL3N sequence, assuming that the start methionine was retained in this recombinant protein. This experiment verifies that the protein we expressed in and purified from *E. coli* was BHL3N. Samples of the other purified proteins were also subjected to N-terminal sequencing. The truncated wild type CI-2 sequence (through four cycles) was Met-Asn-Leu-Lys, as predicted from the DNA sequence. The sequence for BHL1, BHL2, and BHL4 was Met-Lys-Leu-Lys, again confirming the identity of these proteins. The sequence for BHL5, BHL6, and BHL8 was Ala-Lys-Met-Lys, again confirming the identity of these proteins but also revealing that the start methionine was not retained in these three, proteins when expressed in *E. coli*.

c. Mass Spectrometry—All of the purified proteins were subjected to analysis by mass spectrometry. The determined masses and the predicted masses were very similar, further confirming the sequence of the engineered proteins.

Example 3

Addition of Disulfide Bonds

Three pairs of residues (Glu-23 and Arg-81, Thr-22 and Val-82, and Val-53 and Val-70) were identified as candidates for disulfide formation. Constructs designed to substitute Thr-22 and Val-82 (BHL6 residues Thr-6 and Val-66) with cysteines were prepared to make the BHL8 protein. Other constructs were prepared to substitute Thr-22 and Val-82 (BHL3 residues Thr-5 and Val-65) with cysteines, or alternatively, to substitute Glu-23 and Arg-81 (BHL3 residues GLU-6 and Arg-64). Disulfide formation was confirmed in the BHL8 protein by lack of reaction with 5,5'-Dithio-bis (2-Nitrobenzoic acid) (Sigma catalog # D-8130), which would have reacted with free thiols had any been present (Ellman, Arch. Biochem. Biophys. 82:70 (1959), Riddles et al. Meth. Enzym. 91: 49–60 (1983)). Intermolecular disulfide formation in BHL8 was also ruled out because non-reducing SDS-PAGE showed similar mobility for BHL8 and BHL6. Therefore, the BHL8 disulfide was intramolecular, as intended. As will be seen in the following examples, the disulfide bond in BHL8 resulted in an unexpectedly large increase in both proteolytic and thermodynamic stability.

Example 4

Thermodynamic Stability of Engineered Proteins, and Increased Stability Achieved by Addition of a Disulfide Bond The unfolding of CI-2 follows a reversible two-state transition and can be monitored by fluorescence spectroscopy (Jackson and Fersht, Biochemistry 30:10428–10435 (1991)). Similar equilibrium denaturation experiments were done to assess the thermodynamic stability of the engineered proteins of the present study, following the method of Pace et al. (Meth. Enzym. 131:266–280). The engineered or wild-type proteins at a concentration of 2 µM were incubated 18 hours at 25 degrees centigrade in 10 mM sodium phosphate, pH 7.0, with various concentrations of guanidinium chloride. Unfolding of the proteins BHL1, BHL2, BHL3, BHL3N, BHL4, and WT CI-2 were monitored by measuring intrinsic fluorescence at 25 degrees centigrade, using an excitation wavelength of 280 nm and an emission wavelength of 356 nm. BHL5, BHL6, and BHL8 contain multiple tryptophan residues which made it difficult to monitor unfolding by fluorescence techniques. Therefore, the changes in the circular dichroism spectra at 234 nm were used to monitor the unfolding of these proteins. WT CI-2 and BHL4 were again examined using this method. The free energy of unfolding in the absence of denaturant ($\Delta G_{H2O}$) and the guanidium chloride concentration sufficient for 50% unfolding are presented in the following tables.

Equilibrium unfolding parameters (mean±standard deviation). Unfolding was monitored by the change in fluorescence intensity.

| Protein | $\Delta G_{H2O}$ (kcal mol$^{-1}$) | [GdmCl]$_{50\%}$ (M) |
|---|---|---|
| WT Cl-2 | 7.04 ± 0.04 | 3.97 ± 0.01 |
| BHL1 | 4.48 ± 0.34 | 2.36 ± 0.04 |
| BHL2, BHL3, & BHL3N (pooled) | 1.56 ± 0.16 | 0.86 ± 0.02 |
| BHL4 | 4.93 ± 0.19 | 2.59 ± 0.01 |

Equilibrium unfolding parameters (mean±standard deviation). Unfolding was monitored by change in CD spectra at 234 nm.

| Protein | $\Delta G_{H2O}$ (kcal mol$^{-1}$) | [GdmCl]$_{50\%}$ (M) |
|---|---|---|
| WT Cl-2 | 7.52 ± 0.52 | 3.86 ± 0.02 |
| BHL4 | 4.49 ± 0.39 | 2.67 ± 0.01 |
| BHL5 | 2.20 ± 0.23 | 1.32 ± 0.05 |
| BHL6 | 3.09 ± 0.08 | 1.78 ± 0.01 |
| BHL8 | 6.96 ± 0.72 | 3.61 ± 0.02 |
| BHL8 (reduced) | 2.35 ± 0.10 | 1.66 ± 0.02 |

These results show that the disulfide bond of BHL8 unexpectedly led to a significantly increased thermodynamic stability of this protein over the non-disulfide bonded counterpart BHL6. When the experiment was performed with BHL8 that had first been treated with 10 mM dithiothreitol to reduce the disulfide bond, the stability was decreased to a value less than that of BHL6. This confirmed that it was the disulfide bond of BHL8, and not just the two cysteine substitutions, that increased the thermodynamic stability of BHL8 over BHL6.

Example 5

Proteolytic Stability of Engineered Proteins, and Increased Stability Achieved by Addition of a Disulfide Bond Stability of engineered proteins in the presence of proteases such as trypsin or chymotrypsin can provide insights on structural integrity of the proteins. Malfolded proteins tend to be less proteolytically stable than compact, correctly folded proteins. Trypsin and chymotrypsin digests of BHL1, BHL2, BHL3, BHL3N, BHL4, and wild type CI-2 were done for 30 min at 37° C. Three micrograms of WT or engineered CI-2 were incubated with 0.3 µg protease in 100 mM Tris-HCl, 50 mM NaCl, 1 mM CaCl$_2$, pH 8.0, in a volume of 15 µl. Control samples with protease only were incubated in the same buffer. Reactions were stopped by adding an equal volume of Bio-Rad 2x Tris-Tricine SDS sample buffer containing 6 mM PMSF, followed by boiling 5 min. and then analysis by SDS-PAGE. Results are summarized in the following table:

Intact protein detectable after 30 minute incubation with trypsin or chymotrypsin.

| | Trypsin | Chymotrypsin |
|---|---|---|
| Wild type Cl-2 | Yes | Yes |
| BHL1 | Yes | Yes |
| BHL2 | No | No |
| BHL3 | No | No |
| BHL3N | No | No |
| BHL4 | Yes | Yes |

WT CI-2 and BHL1 were resistant to trypsin, and BHL4 was unexpectedly partially resistant, with some intact BHL4 protein remaining after 30 min. The other proteins were completely digested by trypsin into fragments too small to be detected by SDS-PAGE. With respect to chymotrypsin, WT CI-2 was completely resistant, as is to be expected for a chymotrypsin inhibitor. BHL1 and BHL4 were partially resistant whereas derivatives BHL2, BHL3 and BHL3N were completely digested into smaller fragments, with no intact protein remaining.

Using the same buffer and substrate to protease ratio, BHL5, BHL6, BHL8, BHL4, and wild-type CI-2 were incubated with trypsin for 2 min, 4 min, 8 min, 15 min, 30 min, 60 min, or 120 min, or with chymotrypsin for 1 min, 2 min, 4 min, 8 min, 15 min, 30 min, 60 min, or 120 min. Results are summarized in the following table.

Longest time that intact protein still remained during incubation with trypsin or chymotrypsin.

|  | Trypsin | Chymotrypsin |
|---|---|---|
| Wild type CI-2 | 120 min | 120 min |
| BHL4 | 60 min | 120 min |
| BHL5 | <2 min | 1 min |
| BHL6 | 2 min | 4 min |
| BHL8 | 120 min | 120 min |
| BHL8 (reduced) | <2 min | 1 min |

With respect to trypsin, intact protein was still detected for BHL8 and for wild type CI-2 at 120 min., for BHL4 at 60 min, and for BHL6 at 2 min. No BHL5 was detected even at 2 min. With respect to chymotrypsin, intact protein was still detected for wild type CI-2, BHL8, and BHL4 at 120 min., for BHL6 at 4 min., and for BHL5 at 1 min. The same experiment was also done with BHL8 that had first been treated with 10 mM DTT 1 hour at 37 degrees centigrade to reduce the disulfide bond. Reduced BHL8 was not detectable even at 2 min with trypsin, and was detected only at 1 min. with chymotrypsin. This confirms that it is the disulfide bond of BHL8, and not just the cysteine substitutions, that are responsible for the increased proteolytic stability of BHL8 compared to BHL6.

In contrast to the results with BHL8, addition of the same disulfide bond in BHL3 (i.e. between cysteines substituted for Thr-22 and Val-82) did not improve the stability of BHL3 against trypsin. This experiment was done in the same buffer as described above, but with a 1:100 ratio of trypsin to substrate protein, rather than a 1:10 ratio. BHL3 with or without the disulfide was somewhat detectable at 15 min., but not at 60 min.

The relative proteolytic stability of BHL8, BHL4, and BHL1 evident here may prove beneficial. These proteolytically stable proteins may be relatively resistant to plant proteases, which may allow them to accumulate to useful levels in plants. Furthermore, when eaten by ruminants such as cattle or sheep, proteolytically stable proteins may have a better chance of resisting digestion by bacteria in the rumen. The proteins would then be subsequently available to the animal following passage out of the rumen (McNabb et al, J. Sci. Food Agric. 64:53–61 (1994)). The stability against trypsin and chymotrypsin does not necessarily mean that these proteins would be poorly digested by monogastric animals, because the proteins would first have to pass through the stomach, where digestion by pepsin could potentially occur, before they encounter trypsin or chymotrypsin in the intestine.

Example 6

Digestibility of Engineered Proteins in Simulated Gastric Fluid and Simulated Intestinal Fluid Digestion in Simulated Gastric Fluid.

How quickly a protein is digested in simulated gastric fluid may be an indication of how easily digestible it would be in the stomach of an animal or human. Furthermore, proteins that are quickly digested in simulated gastric fluid are less likely to be food allergens than are proteins that are stable in simulated gastric fluid (Astwood et al, Nature Biotechnology 14:1269–1271, (1996)). Digestibility of the BHL proteins was assessed at 37 degrees centigrade in simulated gastric fluid (34 mM NaCl, 0.7% HCl, and 3.2 mg/ml pepsin). Porcine stomach pepsin (Sigma cat # P-6887) was used. Aliquots of the incubation mix containing 3 µg of wild type or engineered CI-2 in 15 to 20 µl were removed at various times and assessed by SDS-PAGE. Time points of 15 sec, 30 sec, 1 min, 5 min, and 30 min were used for wild type CI-2, BHL1, BHL2, BHL3, BHL3N, and BHL4. All of these proteins were digested in simulated gastric fluid within 15 seconds. In separate experiments, time points used for BHL5, BHL6, BHL8, BHL4 (repeat) and wild type CI-2 (repeat) were 30 sec, 1 min, 2 min, 4 min, 8 min, 15 min, and 30 min. All of these proteins were digested in simulated gastric fluid within 30 seconds. It therefore appeared that all of the BHL proteins and wild type CI-2 were easily digested by pepsin in simulated gastric fluid. In contrast to the proteins of the present study, the soybean Kunitz trypsin inhibitor was stable for one hour in simulated gastric fluid (Astwood et al, Nature Biotechnology 14:1269–1271, (1996)).

Digestion in Simulated Intestinal Fluid.

Simulated intestinal fluid was prepared by dissolving 68 mg of monobasic potassium phosphate in 2.5 ml of water, adding 1.9 ml of 0.2 N sodium hydroxide and 4 ml of water. Then 2.0 g porcine pancreatin (Sigma catalog # P-7545) was added and the resulting solution was adjusted with 0.2N sodium hydroxide to a pH of 7.5. Water was added to make a final volume of 10 ml. 50 µl of 1 mg/ml BHL3N or wild-type CI-2 were incubated with 250l µl simulated intestinal fluid at 37 degrees centigrade. At 15 sec, 30 sec, 1 min, 5 min, and 30 min, 40 µl aliquots were removed and added to 40 µl of a stop solution consisting of 2× Tris-Tricine SDS sample buffer (Biorad) containing 2 mM EDTA and 2 mM phenylmethylsulfonyl fluoride (Sigma catalog # P-7626). Digestion was assessed by 16.5% Tris-Tricine SDS-PAGE (precast gels from Biorad). BHL3N was digested by simulated intestinal fluid within 15 seconds. In contrast, wild type CI-2 was resistant to digestion for 30 minutes. This experiment shows that in the intestine of humans or monogastric animals, the intact engineered protein would likely be more digestible than the intact wild type protein would be. Considering the previous experiments with simulated gastric fluid, however, it may be that little of either the wild type or engineered proteins would escape digestion by pepsin in the stomach to reach the intestine intact.

Example 7

Protease Inhibition Assays

The following proteases were used to measure inhibition with CI-2 and the mutants: bovine pancreatic chymotrypsin (Sigma # C-4129), bovine pancreatic trypsin (Sigma # T-8918), porcine pancreatic elastase (Sigma # E-0258), and Subtilisin Carlsberg from *Bacillus licheniformis* (Sigma # P-5380). Assays were done at 37° C. for chymotrypsin, and at 25° C. for the other proteases. Reaction volumes were typically 200 µl and were started by addition of substrate, following preincubation for 15 min with elastase and 30 min with the other proteases. Chymotrypsin and subtilisin assays were done in 200 mM Tris-HCl, pH 8.0, with 1 nM protease and 1 μM WT or engineered CI-2, using 1 mM N-Succinyl-Ala-Ala-Pro-Phe-p Nitroanilide (Sigma #S–7388) as substrate. Trypsin assays were done in 50 mM Tris-HCl, 2 mM NaCl, 2 mM $CaCl_2$, 0.005% TritonX-100, pH 7.5, with 0.5 nM trypsin and 5 μM WT or engineered CI-2. The substrate was 1 mM N-Benzoyl-2-Ile-Glu-Gly-Arg-p-Nitroanilide (Chromogenix S-2222). Elastase assays were done in 200 mM Tris-HCl, pH 8.0 with 50 nM elastase and 2 μM WT or engineered CI-2. The substrate was 1 mM N-succinyl-Ala-Ala-Ala-p-Nitroanilide (Sigma #S-4760). The linear increase in absorbance at 405 nm was monitored over time. Activities in the presence of WT or engineered CI-2 were expressed as a percentage of the activity of the uninhibited proteases. The results are summarized in the following table.

Protease activity in the presence of WT or engineered CI-2. Values are expressed as a percent of control assays containing no WT or engineered CI-2 (mean±standard deviation).

| | Protease activity (% of control) | | | |
|---|---|---|---|---|
| Protein | Chymotrypsin | Subtilisin | Trypsin | Elastase |
| WT CI-2 | 9 ± 4 | 0.3 ± 0.4 | 105 ± 6 | 3 ± 1 |
| BHL1 | 87 ± 6 | 15 ± 2 | 14 ± 4 | 104 ± 5 |
| BHL2 | 97 ± 13 | 82 ± 5 | 91 ± 8 | 107 ± 5 |
| BHL3 | 102 ± 5 | 101 ± 9 | 104 ± 6 | 107 ± 7 |
| BHL3N | 98 ± 10 | 96 ± 2 | 108 ± 4 | 105 ± 5 |
| BHL4 | 73 ± 10 | 50 ± 3 | 100 ± 4 | 104 ± 11 |
| BHL5 | 101 ± 8 | 57 ± 8 | 101 ± 13 | 106 ± 0.1 |
| BHL6 | 101 ± 8 | 37 ± 3 | 98 ± 2 | 109 ± 4 |
| BHL8 | 102 ± 7 | 35 ± 1 | 111 ± 4 | 107 ± 2 |

The wild type protein was an effective inhibitor of chymotrypsin, subtilisin, and elastase, but not of trypsin, consistent with a previous study (Longstaff et al., Biochemistry 29:7339–7347, (1990)). Compared to wild type CI-2, the engineered proteins have reduced inhibitory activity against chymotrypsin, subtilisin, and elastase. Except for BHL1, the engineered proteins also are not effective inhibitors of trypsin. A further experiment was done with BHL4. This protein was first digested with pepsin for 30 seconds, and then the inhibitory activity of the peptic fragments was assessed against chymotrypsin or subtilisin. The BHL4 peptic fragments retained no inhibitory activity against either chymotrypsin or subtilisin.

Example 8

Protein Conformation Analysis of Engineered Proteins by Circular Dichroism

The wild-type and engineered proteins were analyzed by far UV circular dichroism (CD) spectroscopy in 10 mM sodium phosphate, pH 7. The CD spectra for BHL1, BHL2, BHL3, BHL3N, and BHL4 were very similar to that of wild-type CI-2, suggesting that these proteins have similar secondary structures. The spectra for BHL5, BHL6, and BHL8 were also similar overall to the WT CI-2 spectrum, but with detectable increases in ellipticity values for BHL5 and BHL8. The wild-type protein and BHL5, BHL6, and BHL8 were also analyzed by near UV (250 nm to 350 nm) circular dichroism spectroscopy. Differences in the BHL8 spectrum were detected relative to the others.

Example 9

Analysis of Engineered Proteins by Fluorescence Quenching an emission Acrylamide effectively quenches the fluorescence of accessible tryptophan residues in proteins. We examined fluorescence quenching of the single tryptophan residue of BHL1, BHL2, BHL3, BHL4, and wild-type CI-2 in the presence or absence of 6M guanidinium chloride. The quenching of intrinsic fluorescence of the proteins was followed by sequential addition of small aliquots of a 1 M acrylamide solution. The excitation wavelength was set at 295 nm to ensure optimal absorption by the tryptophan residue. In the absence of denaturant wavelength of 337 nm and a protein concentration of 20 μM were used. In the presence of 6 M guanidinium chloride, the emission wavelength was 356 nm and the protein concentration was lowered to 2 μM because of the increase in the quantum yield of fluorescence after denaturation. The fluorescence intensities were corrected for the self-absorption of incident light [McClure and Edelman, Biochemistry 6:567–572, (1967)) by using a molar extinction coefficient of 0.23 for acrylamide [Parker, "Photoluminescence of Solutions", Elsevier, N.Y., (1968)). The quenching data were plotted as a direct Stern-Volmer plot, $F_0/F$ vs the molar concentration of acrylamide, where $F_0$ is the fluorescence intensity in the absence of quencher and F is the fluorescence intensity in the presence of quencher. The Stern-Volmer quenching constant $K_{sv}$ was determined from the slope of this plot, and is summarized in the following table.

Stern-Volmer constants determined by acrylamide quenching of tryptophan fluorescence in the absence of denaturant (mean±standard deviation).

| Protein | Ksv (M$^{-1}$) |
|---|---|
| WT CI-2 | 1.7 ± 0.1 |
| BHL1 | 3.5 ± 0.3 |
| BHL2, BHL3N | 5.5 ± 0.4 |
| BHL3 | 2.4 ± 0.2 |
| BHL4 | 0.65 ± 0.02 |

This experiment revealed that, in the absence of denaturant, there are differences in the accessibility of the tryptophan among these proteins. In contrast, the tryptophan was more completely accessible in all of the proteins upon unfolding in 6M guanidinium chloride (average Ksv of approximately 17 M.$^{-1}$).

Example 10

Analysis of Engineered Proteins by Western Blots

Rabbit polyclonal antibodies (two rabbits for each) were prepared against truncated wild type CI-2, BHL1, or a 1:1 mixture of BHL6 and BHL8. Western blots of 100 ng of each protein were probed with a 1:1000 dilution of antisera against wild type CI-2 or against the BHL6/BHL8 mixture. Antisera to wild type CI-2 reacted weakly with BHL5, BHL6, and BHL8, and reacted more strongly with all of the other BHL proteins and with wild type CI-2. Antibodies against the BHL6/BHL8 mixture reacted most strongly with BHL 5, BHL6, and BHL8, but reacted less strongly with the other BHL proteins and with wild-type CI-2. Other western blots revealed that antisera against BHL1 recognized wild type CI-2, BHL1, BHL2, BHL3, BHL3N, BHL4, BHL5, and BHL6.

```
                   65                  70                  75                  80
agg gtc ggc                                                                                    249
Arg Val Gly <210> SEQ ID NO 2
<211> LENGTH: 83
<212> TYPE: PRT
<213> ORGANISM: Hordeum vulgare

<400> SEQUENCE: 2

Ser Ser Val Glu Lys Lys Pro Glu Gly Val Asn Thr Gly Ala Gly Asp
 1               5                  10                  15

Arg His Asn Leu Lys Thr Glu Trp Pro Glu Leu Val Gly Lys Ser Val
             20                  25                  30

Glu Glu Ala Lys Lys Val Ile Leu Gln Asp Lys Pro Glu Ala Gln Ile
         35                  40                  45

Ile Val Leu Pro Val Gly Thr Ile Val Thr Met Glu Tyr Arg Ile Asp
     50                  55                  60

Arg Val Arg Leu Phe Val Asp Lys Leu Asp Asn Ile Ala Gln Val Pro
 65                  70                  75                  80

Arg Val Gly

<210> SEQ ID NO 3
<211> LENGTH: 198
<212> TYPE: DNA
<213> ORGANISM: Hordeum vulgare
<220> FEATURE:
<221> NAME/KEY: CDS
<222> LOCATION: (1)...(198)

<400> SEQUENCE: 3 atg aac ctg aag aca gag tgg cca gag ttg gtg ggg aaa tcg gtg gag     48
Met Asn Leu Lys Thr Glu Trp Pro Glu Leu Val Gly Lys Ser Val Glu
 1               5                  10                  15 gag gcc aag aag gtg att ctg cag gac aag cca gag gcg caa atc ata     96
Glu Ala Lys Lys Val Ile Leu Gln Asp Lys Pro Glu Ala Gln Ile Ile
             20                  25                  30 gtt cta ccg gtg ggg aca att gtg acc atg gaa tat cgg atc gac cgc    144
Val Leu Pro Val Gly Thr Ile Val Thr Met Glu Tyr Arg Ile Asp Arg
         35                  40                  45 gtc cgc ctc ttt gtc gat aaa ctc gac aac att gcc cag gtc ccc agg    192
Val Arg Leu Phe Val Asp Lys Leu Asp Asn Ile Ala Gln Val Pro Arg
     50                  55                  60 gtc ggc                                                            198
Val Gly
 65

<210> SEQ ID NO 4
<211> LENGTH: 66
<212> TYPE: PRT
<213> ORGANISM: Hordeum vulgare

<400> SEQUENCE: 4

Met Asn Leu Lys Thr Glu Trp Pro Glu Leu Val Gly Lys Ser Val Glu
 1               5                  10                  15

Glu Ala Lys Lys Val Ile Leu Gln Asp Lys Pro Glu Ala Gln Ile Ile
             20                  25                  30

Val Leu Pro Val Gly Thr Ile Val Thr Met Glu Tyr Arg Ile Asp Arg
         35                  40                  45

Val Arg Leu Phe Val Asp Lys Leu Asp Asn Ile Ala Gln Val Pro Arg
```

-continued

```
             50                  55                  60
Val Gly
 65

<210> SEQ ID NO 5
<211> LENGTH: 198
<212> TYPE: DNA
<213> ORGANISM: Hordeum vulgare
<220> FEATURE:
<221> NAME/KEY: CDS
<222> LOCATION: (1)...(198)

<400> SEQUENCE: 5 atg aag ctg aag aca gag tgg ccg gag ttg gtg ggg aaa tcg gtg gag      48
Met Lys Leu Lys Thr Glu Trp Pro Glu Leu Val Gly Lys Ser Val Glu
  1               5                  10                  15 aaa gcc aag aag gtg atc ctg aag gac aag cca gag gcg caa atc ata      96
Lys Ala Lys Lys Val Ile Leu Lys Asp Lys Pro Glu Ala Gln Ile Ile
             20                  25                  30 gtt ctg ccg gtt ggt aca aag gtg acg aag gaa tat aag atc gac cgc     144
Val Leu Pro Val Gly Thr Lys Val Thr Lys Glu Tyr Lys Ile Asp Arg
         35                  40                  45 gtc aag ctc ttt gtg gat aaa aag gac aac atc gcg cag gtc ccc agg     192
Val Lys Leu Phe Val Asp Lys Lys Asp Asn Ile Ala Gln Val Pro Arg
     50                  55                  60 gtc ggc                                                             198
Val Gly
 65

<210> SEQ ID NO 6
<211> LENGTH: 66
<212> TYPE: PRT
<213> ORGANISM: Hordeum vulgare

<400> SEQUENCE: 6

Met Lys Leu Lys Thr Glu Trp Pro Glu Leu Val Gly Lys Ser Val Glu
  1               5                  10                  15

Lys Ala Lys Lys Val Ile Leu Lys Asp Lys Pro Glu Ala Gln Ile Ile
             20                  25                  30

Val Leu Pro Val Gly Thr Lys Val Thr Lys Glu Tyr Lys Ile Asp Arg
         35                  40                  45

Val Lys Leu Phe Val Asp Lys Lys Asp Asn Ile Ala Gln Val Pro Arg
     50                  55                  60

Val Gly
 65

<210> SEQ ID NO 7
<211> LENGTH: 198
<212> TYPE: DNA
<213> ORGANISM: Hordeum vulgare
<220> FEATURE:
<221> NAME/KEY: CDS
<222> LOCATION: (1)...(198)

<400> SEQUENCE: 7 atg aag ctg aag aca gag tgg ccg gag ttg gtg ggg aaa tcg gtg gag      48
Met Lys Leu Lys Thr Glu Trp Pro Glu Leu Val Gly Lys Ser Val Glu
  1               5                  10                  15 aaa gcc aag aag gtg atc ctg aag gac aag cca gag gcg caa atc ata      96
Lys Ala Lys Lys Val Ile Leu Lys Asp Lys Pro Glu Ala Gln Ile Ile
             20                  25                  30 gtt cta ccg gtt ggt aca aag gtg gcg aag gcc tat aag atc gac aag     144
```

```
Val Leu Pro Val Gly Thr Lys Val Ala Lys Ala Tyr Lys Ile Asp Lys
         35                  40                  45 gtc aag ctt ttt gtg gat aaa aag gac aac atc gcg cag gtc ccc agg    192
Val Lys Leu Phe Val Asp Lys Lys Asp Asn Ile Ala Gln Val Pro Arg
 50                  55                  60 gtc ggc                                                             198
Val Gly
 65

<210> SEQ ID NO 8
<211> LENGTH: 66
<212> TYPE: PRT
<213> ORGANISM: Hordeum vulgare

<400> SEQUENCE: 8

Met Lys Leu Lys Thr Glu Trp Pro Glu Leu Val Gly Lys Ser Val Glu
 1               5                  10                  15

Lys Ala Lys Lys Val Ile Leu Lys Asp Lys Pro Glu Ala Gln Ile Ile
             20                  25                  30

Val Leu Pro Val Gly Thr Lys Val Ala Lys Ala Tyr Lys Ile Asp Lys
         35                  40                  45

Val Lys Leu Phe Val Asp Lys Lys Asp Asn Ile Ala Gln Val Pro Arg
 50                  55                  60

Val Gly
 65

<210> SEQ ID NO 9
<211> LENGTH: 198
<212> TYPE: DNA
<213> ORGANISM: Hordeum vulgare
<220> FEATURE:
<221> NAME/KEY: CDS
<222> LOCATION: (1)...(198)

<400> SEQUENCE: 9 atg aag ctg aag aca gag tgg ccg gag ttg gtg ggg aaa tcg gtg gag    48
Met Lys Leu Lys Thr Glu Trp Pro Glu Leu Val Gly Lys Ser Val Glu
 1               5                  10                  15 aaa gcc aag aag gtg atc ctg aag gac aag cca gag gcg caa atc ata    96
Lys Ala Lys Lys Val Ile Leu Lys Asp Lys Pro Glu Ala Gln Ile Ile
             20                  25                  30 gtt cta ccg gtt ggt aca aag gtg ggt aag cat tat aag atc gac aag   144
Val Leu Pro Val Gly Thr Lys Val Gly Lys His Tyr Lys Ile Asp Lys
         35                  40                  45 gtc aag ctt ttt gtg gat aaa aag gac aac atc gcg cag gtc ccc agg    192
Val Lys Leu Phe Val Asp Lys Lys Asp Asn Ile Ala Gln Val Pro Arg
 50                  55                  60 gtc ggc                                                             198
Val Gly
 65

<210> SEQ ID NO 10
<211> LENGTH: 66
<212> TYPE: PRT
<213> ORGANISM: Hordeum vulgare

<400> SEQUENCE: 10

Met Lys Leu Lys Thr Glu Trp Pro Glu Leu Val Gly Lys Ser Val Glu
 1               5                  10                  15

Lys Ala Lys Lys Val Ile Leu Lys Asp Lys Pro Glu Ala Gln Ile Ile
             20                  25                  30
```

```
Val Leu Pro Val Gly Thr Lys Val Gly Lys His Tyr Lys Ile Asp Lys
         35                  40                  45

Val Lys Leu Phe Val Asp Lys Asp Asn Ile Ala Gln Val Pro Arg
     50                  55                  60

Val Gly
65

<210> SEQ ID NO 11
<211> LENGTH: 252
<212> TYPE: DNA
<213> ORGANISM: Hordeum vulgare
<220> FEATURE:
<221> NAME/KEY: CDS
<222> LOCATION: (1)...(252)

<400> SEQUENCE: 11 atg aag tcg gtg gag aag aaa ccg aag ggt gtg aag aca ggt gcg ggt      48
Met Lys Ser Val Glu Lys Lys Pro Lys Gly Val Lys Thr Gly Ala Gly
  1               5                  10                  15 gac aag cat aag ctg aag aca gag tgg ccg gag ttg gtg ggg aaa tcg      96
Asp Lys His Lys Leu Lys Thr Glu Trp Pro Glu Leu Val Gly Lys Ser
             20                  25                  30 gtg gag aaa gcc aag aag gtg atc ctg aag gac aag cca gag gcg caa     144
Val Glu Lys Ala Lys Lys Val Ile Leu Lys Asp Lys Pro Glu Ala Gln
         35                  40                  45 atc ata gtt cta ccg gtt ggt aca aag gtg ggt aag cat tat aag atc     192
Ile Ile Val Leu Pro Val Gly Thr Lys Val Gly Lys His Tyr Lys Ile
     50                  55                  60 gac aag gtc aag ctt ttt gtg gat aaa aag gac aac atc gcg cag gtc     240
Asp Lys Val Lys Leu Phe Val Asp Lys Lys Asp Asn Ile Ala Gln Val
 65                  70                  75                  80 ccc agg gtc ggc                                                     252
Pro Arg Val Gly <210> SEQ ID NO 12
<211> LENGTH: 84
<212> TYPE: PRT
<213> ORGANISM: Hordeum vulgare

<400> SEQUENCE: 12

Met Lys Ser Val Glu Lys Lys Pro Lys Gly Val Lys Thr Gly Ala Gly
  1               5                  10                  15

Asp Lys His Lys Leu Lys Thr Glu Trp Pro Glu Leu Val Gly Lys Ser
             20                  25                  30

Val Glu Lys Ala Lys Lys Val Ile Leu Lys Asp Lys Pro Glu Ala Gln
         35                  40                  45

Ile Ile Val Leu Pro Val Gly Thr Lys Val Gly Lys His Tyr Lys Ile
     50                  55                  60

Asp Lys Val Lys Leu Phe Val Asp Lys Lys Asp Asn Ile Ala Gln Val
 65                  70                  75                  80

Pro Arg Val Gly

<210> SEQ ID NO 13
<211> LENGTH: 198
<212> TYPE: DNA
<213> ORGANISM: Hordeum vulgare
<220> FEATURE:
<221> NAME/KEY: CDS
<222> LOCATION: (1)...(198)

<400> SEQUENCE: 13
```

```
atg aag ctg aag aca gag tgg ccg gag ttg gtg ggg aaa tcg gtg gag      48
Met Lys Leu Lys Thr Glu Trp Pro Glu Leu Val Gly Lys Ser Val Glu
 1               5                  10                  15 aaa gcc aag aag gtg atc ctg aag gac aag cca gag gcg caa atc ata      96
Lys Ala Lys Lys Val Ile Leu Lys Asp Lys Pro Glu Ala Gln Ile Ile
                 20                  25                  30 gtt cta ccg gtt ggt aca aag gtg acg ggc gaa tac aag atc gac cgc     144
Val Leu Pro Val Gly Thr Lys Val Thr Gly Glu Tyr Lys Ile Asp Arg
             35                  40                  45 gtc aag ctt ttt gtg gat aaa aag gac aac atc gcg cag gtc ccc agg     192
Val Lys Leu Phe Val Asp Lys Lys Asp Asn Ile Ala Gln Val Pro Arg
 50                  55                  60 gtc ggc                                                              198
Val Gly
 65

<210> SEQ ID NO 14
<211> LENGTH: 66
<212> TYPE: PRT
<213> ORGANISM: Hordeum vulgare

<400> SEQUENCE: 14

Met Lys Leu Lys Thr Glu Trp Pro Glu Leu Val Gly Lys Ser Val Glu
 1               5                  10                  15

Lys Ala Lys Lys Val Ile Leu Lys Asp Lys Pro Glu Ala Gln Ile Ile
                 20                  25                  30

Val Leu Pro Val Gly Thr Lys Val Thr Gly Glu Tyr Lys Ile Asp Arg
             35                  40                  45

Val Lys Leu Phe Val Asp Lys Lys Asp Asn Ile Ala Gln Val Pro Arg
 50                  55                  60

Val Gly
 65

<210> SEQ ID NO 15
<211> LENGTH: 201
<212> TYPE: DNA
<213> ORGANISM: Hordeum vulgare
<220> FEATURE:
<221> NAME/KEY: CDS
<222> LOCATION: (1)...(201)

<400> SEQUENCE: 15 atg gct aag atg aag aca acg tgg cct gag ctg gtg ggc aag acc gtg      48
Met Ala Lys Met Lys Thr Thr Trp Pro Glu Leu Val Gly Lys Thr Val
 1               5                  10                  15 gag aaa gcc aag aag atg atc atg aag gac aag cca gag gcg aag atc      96
Glu Lys Ala Lys Lys Met Ile Met Lys Asp Lys Pro Glu Ala Lys Ile
                 20                  25                  30 atg gtt ctg cca gtt ggg acc aaa gtg acc ggt gaa tgg aag atg gat     144
Met Val Leu Pro Val Gly Thr Lys Val Thr Gly Glu Trp Lys Met Asp
             35                  40                  45 cgc gtc aaa ctc tgg gtc gac aag aag gac aag atc gcc aag act ccg     192
Arg Val Lys Leu Trp Val Asp Lys Lys Asp Lys Ile Ala Lys Thr Pro
 50                  55                  60 aag gtc ggc                                                          201
Lys Val Gly
 65

<210> SEQ ID NO 16
<211> LENGTH: 67
<212> TYPE: PRT
<213> ORGANISM: Hordeum vulgare
```

<400> SEQUENCE: 16

| Met | Ala | Lys | Met | Lys | Thr | Thr | Trp | Pro | Glu | Leu | Val | Gly | Lys | Thr | Val |
|---|---|---|---|---|---|---|---|---|---|---|---|---|---|---|---|
| 1 | | | | 5 | | | | | 10 | | | | | 15 | |

| Glu | Lys | Ala | Lys | Lys | Met | Ile | Met | Lys | Asp | Lys | Pro | Glu | Ala | Lys | Ile |
|---|---|---|---|---|---|---|---|---|---|---|---|---|---|---|---|
| | | | 20 | | | | | 25 | | | | | 30 | | |

| Met | Val | Leu | Pro | Val | Gly | Thr | Lys | Val | Thr | Gly | Glu | Trp | Lys | Met | Asp |
|---|---|---|---|---|---|---|---|---|---|---|---|---|---|---|---|
| | | 35 | | | | | 40 | | | | | 45 | | | |

| Arg | Val | Lys | Leu | Trp | Val | Asp | Lys | Lys | Asp | Lys | Ile | Ala | Lys | Thr | Pro |
|---|---|---|---|---|---|---|---|---|---|---|---|---|---|---|---|
| | 50 | | | | | 55 | | | | | 60 | | | | |

Lys Val Gly
65

<210> SEQ ID NO 17
<211> LENGTH: 201
<212> TYPE: DNA
<213> ORGANISM: Hordeum vulgare
<220> FEATURE:
<221> NAME/KEY: CDS
<222> LOCATION: (1)...(201)

<400> SEQUENCE: 17

| atg | gct | aag | atg | aag | aca | acg | tgg | cct | gag | ctg | gtg | ggc | aag | acc | gtg | 48 |
|---|---|---|---|---|---|---|---|---|---|---|---|---|---|---|---|---|
| Met | Ala | Lys | Met | Lys | Thr | Thr | Trp | Pro | Glu | Leu | Val | Gly | Lys | Thr | Val | |
| 1 | | | | 5 | | | | | 10 | | | | | 15 | | |

| gag | aaa | gcc | aag | aag | atg | atc | atg | aag | gac | aag | cca | gag | gcg | aag | atc | 96 |
|---|---|---|---|---|---|---|---|---|---|---|---|---|---|---|---|---|
| Glu | Lys | Ala | Lys | Lys | Met | Ile | Met | Lys | Asp | Lys | Pro | Glu | Ala | Lys | Ile | |
| | | | 20 | | | | | 25 | | | | | 30 | | | |

| atg | gtt | ctg | cca | gtt | ggg | acc | aaa | gtg | acc | ggt | gaa | tgg | aag | atg | gat | 144 |
|---|---|---|---|---|---|---|---|---|---|---|---|---|---|---|---|---|
| Met | Val | Leu | Pro | Val | Gly | Thr | Lys | Val | Thr | Gly | Glu | Trp | Lys | Met | Asp | |
| | | 35 | | | | | 40 | | | | | 45 | | | | |

| cgc | gtc | cgc | ctc | tgg | gtc | gac | aag | aag | gac | aag | atc | gcc | aag | act | ccg | 192 |
|---|---|---|---|---|---|---|---|---|---|---|---|---|---|---|---|---|
| Arg | Val | Arg | Leu | Trp | Val | Asp | Lys | Lys | Asp | Lys | Ile | Ala | Lys | Thr | Pro | |
| | 50 | | | | | 55 | | | | | 60 | | | | | |

| aag | gtc | ggc | | | | | | | | | | | | | | 201 |
|---|---|---|---|---|---|---|---|---|---|---|---|---|---|---|---|---|
| Lys | Val | Gly | | | | | | | | | | | | | | |
| 65 | | | | | | | | | | | | | | | | |

<210> SEQ ID NO 18
<211> LENGTH: 67
<212> TYPE: PRT
<213> ORGANISM: Hordeum vulgare

<400> SEQUENCE: 18

| Met | Ala | Lys | Met | Lys | Thr | Thr | Trp | Pro | Glu | Leu | Val | Gly | Lys | Thr | Val |
|---|---|---|---|---|---|---|---|---|---|---|---|---|---|---|---|
| 1 | | | | 5 | | | | | 10 | | | | | 15 | |

| Glu | Lys | Ala | Lys | Lys | Met | Ile | Met | Lys | Asp | Lys | Pro | Glu | Ala | Lys | Ile |
|---|---|---|---|---|---|---|---|---|---|---|---|---|---|---|---|
| | | | 20 | | | | | 25 | | | | | 30 | | |

| Met | Val | Leu | Pro | Val | Gly | Thr | Lys | Val | Thr | Gly | Glu | Trp | Lys | Met | Asp |
|---|---|---|---|---|---|---|---|---|---|---|---|---|---|---|---|
| | | 35 | | | | | 40 | | | | | 45 | | | |

| Arg | Val | Arg | Leu | Trp | Val | Asp | Lys | Lys | Asp | Lys | Ile | Ala | Lys | Thr | Pro |
|---|---|---|---|---|---|---|---|---|---|---|---|---|---|---|---|
| | 50 | | | | | 55 | | | | | 60 | | | | |

Lys Val Gly
65

<210> SEQ ID NO 19
<211> LENGTH: 201
<212> TYPE: DNA
<213> ORGANISM: Hordeum vulgare
<220> FEATURE:
<221> NAME/KEY: CDS -continued

```
<222> LOCATION: (1)...(201)

<400> SEQUENCE: 19 atg gct aag atg aag tgc acg tgg cct gag ctg gtg ggc aag acc gtg      48
Met Ala Lys Met Lys Cys Thr Trp Pro Glu Leu Val Gly Lys Thr Val
 1               5                  10                  15 gag aaa gcc aag aag atg atc atg aag gac aag cca gag gcg aag atc      96
Glu Lys Ala Lys Lys Met Ile Met Lys Asp Lys Pro Glu Ala Lys Ile
            20                  25                  30 atg gtt ctg cca gtt ggg acc aaa gtg acc ggt gaa tgg aag atg gat     144
Met Val Leu Pro Val Gly Thr Lys Val Thr Gly Glu Trp Lys Met Asp
        35                  40                  45 cgc gtc cgc ctc tgg gtc gac aag aag gac aag atc gcc aag act ccg     192
Arg Val Arg Leu Trp Val Asp Lys Lys Asp Lys Ile Ala Lys Thr Pro
    50                  55                  60 aag tgc ggc                                                          201
Lys Cys Gly
 65

<210> SEQ ID NO 20
<211> LENGTH: 67
<212> TYPE: PRT
<213> ORGANISM: Hordeum vulgare

<400> SEQUENCE: 20

Met Ala Lys Met Lys Cys Thr Trp Pro Glu Leu Val Gly Lys Thr Val
 1               5                  10                  15

Glu Lys Ala Lys Lys Met Ile Met Lys Asp Lys Pro Glu Ala Lys Ile
            20                  25                  30

Met Val Leu Pro Val Gly Thr Lys Val Thr Gly Glu Trp Lys Met Asp
        35                  40                  45

Arg Val Arg Leu Trp Val Asp Lys Lys Asp Lys Ile Ala Lys Thr Pro
    50                  55                  60

Lys Cys Gly
 65

<210> SEQ ID NO 21
<211> LENGTH: 18
<212> TYPE: DNA
<213> ORGANISM: Artificial Sequence
<220> FEATURE:
<223> OTHER INFORMATION: Primer based on Hordeum vulgare

<400> SEQUENCE: 21
atgaagtcgg tggagaag                                                   18

<210> SEQ ID NO 22
<211> LENGTH: 18
<212> TYPE: DNA
<213> ORGANISM: Artificial Sequence
<220> FEATURE:
<223> OTHER INFORMATION: Primer based on Hordeum vulgare

<400> SEQUENCE: 22
gccgaccctg gggacctg                                                   18

<210> SEQ ID NO 23
<211> LENGTH: 459
<212> TYPE: DNA
<213> ORGANISM: Zea mays
<220> FEATURE:
<221> NAME/KEY: CDS
<222> LOCATION: (1)...(288)
```

-continued

```
<220> FEATURE:
<221> NAME/KEY: misc_feature
<222> LOCATION: (1)...(459)
<223> OTHER INFORMATION: n = A,T,C or G

<400> SEQUENCE: 23 gca gtg caa caa gca aga ttt acc tgc cca tcg atc ata tcg tca act      48
Ala Val Gln Gln Ala Arg Phe Thr Cys Pro Ser Ile Ile Ser Ser Thr
 1               5                  10                  15 ggt ccg gca gtt cgc gac acc atg agc tcc acg gag tgc ggc ggc ggc      96
Gly Pro Ala Val Arg Asp Thr Met Ser Ser Thr Glu Cys Gly Gly Gly
                20                  25                  30 ggc ggc ggc gcc aag acg tcg tgg cct gag gtg gtc ggg ctg agc gtg     144
Gly Gly Gly Ala Lys Thr Ser Trp Pro Glu Val Val Gly Leu Ser Val
         35                  40                  45 gag gac gcc aag aag gtg atg gtc aag gac aag ccg gac gcc gac atc     192
Glu Asp Ala Lys Lys Val Met Val Lys Asp Lys Pro Asp Ala Asp Ile
 50                  55                  60 gtg gtg ctg ccc gtc ggc tcc gtg gtg acc gcg gat tat cgc cct aac     240
Val Val Leu Pro Val Gly Ser Val Val Thr Ala Asp Tyr Arg Pro Asn
 65                  70                  75                  80 cgt gtc cgc atc ttc gtc gac atc gtc gcc cag acg ccc cac atc ggc     288
Arg Val Arg Ile Phe Val Asp Ile Val Ala Gln Thr Pro His Ile Gly
                 85                  90                  95 tgataatata taagctagcc gctatttcct ttccttgccc cagaacttga aataaatata    348
tatacgatga ataacgcgg gcatgccgaa tanatggant gtgnntgaat tctcactaat    408
taagtaatgn cataaataaa cgtattcaaa aaaaaaaaaa aaaaaaaaaa a            459

<210> SEQ ID NO 24
<211> LENGTH: 96
<212> TYPE: PRT
<213> ORGANISM: Zea mays

<400> SEQUENCE: 24

Ala Val Gln Gln Ala Arg Phe Thr Cys Pro Ser Ile Ile Ser Ser Thr
 1               5                  10                  15

Gly Pro Ala Val Arg Asp Thr Met Ser Ser Thr Glu Cys Gly Gly Gly
                20                  25                  30

Gly Gly Gly Ala Lys Thr Ser Trp Pro Glu Val Val Gly Leu Ser Val
         35                  40                  45

Glu Asp Ala Lys Lys Val Met Val Lys Asp Lys Pro Asp Ala Asp Ile
 50                  55                  60

Val Val Leu Pro Val Gly Ser Val Val Thr Ala Asp Tyr Arg Pro Asn
 65                  70                  75                  80

Arg Val Arg Ile Phe Val Asp Ile Val Ala Gln Thr Pro His Ile Gly
                 85                  90                  95

<210> SEQ ID NO 25
<211> LENGTH: 428
<212> TYPE: DNA
<213> ORGANISM: Zea mays
<220> FEATURE:
<221> NAME/KEY: CDS
<222> LOCATION: (1)...(303)

<400> SEQUENCE: 25 cga ccc acg cgt ccg ccc acg cgt ccg gca aga ttt acc tgc cca tcg      48
Arg Pro Thr Arg Pro Pro Thr Arg Pro Ala Arg Phe Thr Cys Pro Ser
 1               5                  10                  15 atc ata tcg tca act ggt ccg gca gtt cgc gac acc atg agc tcc acg      96
```

```
                                                                                  -continued Ile Ile Ser Ser Thr Gly Pro Ala Val Arg Asp Thr Met Ser Ser Thr
         20                  25                  30 gag tgc ggc ggc ggc ggc ggc gcc aag acg tcg tgg cct gag gtg          144
Glu Cys Gly Gly Gly Gly Gly Ala Lys Thr Ser Trp Pro Glu Val
     35                  40                  45 gtc ggg ctg agc gtg gag gac gcc aag aag gtg atc ctc aag gac aag      192
Val Gly Leu Ser Val Glu Asp Ala Lys Lys Val Ile Leu Lys Asp Lys
 50                  55                  60 ccg gac gcc gac atc gtg gtg ctg ccc gtc ggc tcc gtg gtg acc gcg      240
Pro Asp Ala Asp Ile Val Val Leu Pro Val Gly Ser Val Val Thr Ala
 65                  70                  75                  80 gat tat cgc cct aac cgt gtc cgc atc ttc gtc gac atc gtc gcc cag      288
Asp Tyr Arg Pro Asn Arg Val Arg Ile Phe Val Asp Ile Val Ala Gln
                 85                  90                  95 acg ccc cac atc ggc tgataatata taagctagcc gctatttcct ttccttgccc      343
Thr Pro His Ile Gly
            100 cagaacttga aataaatata tatacgatga ataacgcgg gcatgccgaa taatggatgt     403 gtgaaaaaaa aaaaaaaaaa aaaaa                                          428

<210> SEQ ID NO 26
<211> LENGTH: 101
<212> TYPE: PRT
<213> ORGANISM: Zea mays

<400> SEQUENCE: 26

Arg Pro Thr Arg Pro Pro Thr Arg Pro Ala Arg Phe Thr Cys Pro Ser
 1               5                  10                  15

Ile Ile Ser Ser Thr Gly Pro Ala Val Arg Asp Thr Met Ser Ser Thr
                 20                  25                  30

Glu Cys Gly Gly Gly Gly Gly Ala Lys Thr Ser Trp Pro Glu Val
         35                  40                  45

Val Gly Leu Ser Val Glu Asp Ala Lys Lys Val Ile Leu Lys Asp Lys
 50                  55                  60

Pro Asp Ala Asp Ile Val Val Leu Pro Val Gly Ser Val Val Thr Ala
65                  70                  75                  80

Asp Tyr Arg Pro Asn Arg Val Arg Ile Phe Val Asp Ile Val Ala Gln
                 85                  90                  95

Thr Pro His Ile Gly
            100

<210> SEQ ID NO 27
<211> LENGTH: 441
<212> TYPE: DNA
<213> ORGANISM: Zea mays
<220> FEATURE:
<221> NAME/KEY: CDS
<222> LOCATION: (1)...(255)
<220> FEATURE:
<221> NAME/KEY: misc_feature
<222> LOCATION: (1)...(441)
<223> OTHER INFORMATION: n = A,T,C or G

<400> SEQUENCE: 27 tta att att gcc ctt tca gtt ngc cat cgg cag ccg agc acc atg agc      48
Leu Ile Ile Ala Leu Ser Val Xaa His Arg Gln Pro Ser Thr Met Ser
 1               5                  10                  15 tcc aca ggc ggc ggc gac gat ggc gcc aag aag tct tgg ccg gaa gtg     96
Ser Thr Gly Gly Gly Asp Asp Gly Ala Lys Lys Ser Trp Pro Glu Val
                 20                  25                  30
```

```
gtc ggg ctc agc ctg gaa gaa gcc aag agg gtg atc ctg tgc gac aag       144
Val Gly Leu Ser Leu Glu Glu Ala Lys Arg Val Ile Leu Cys Asp Lys
            35                  40                  45 ccc gac gcc gac atc gtc gtg ctg ccc gtc ggc acg ccg gtg acc atg       192
Pro Asp Ala Asp Ile Val Val Leu Pro Val Gly Thr Pro Val Thr Met
 50                  55                  60 gat ttc cgc ccc aac cgc gtc cgc atc ttc gtc gac acc gtc gcg gag       240
Asp Phe Arg Pro Asn Arg Val Arg Ile Phe Val Asp Thr Val Ala Glu
 65                  70                  75                  80 gca mcc cac atc ggc tgaggttaaa tctacaaaat gaatgaytcg gacatgccat       295
Ala Xaa His Ile Gly
                85 gcgtacntgt ccgtcgccga ataatggatg tgtgtgtgct tcgatcgttc ctaataagtt     355 gctagtnaaa aataatnggc atcgtcgtta ntgcatgaat aaaaagtatc agaataatgt     415 tcacccttc naaaaaaaaa aaaaa                                            441

<210> SEQ ID NO 28
<211> LENGTH: 85
<212> TYPE: PRT
<213> ORGANISM: Zea mays
<220> FEATURE:
<221> NAME/KEY: VARIANT
<222> LOCATION: (1)...(85)
<223> OTHER INFORMATION: Xaa = Any Amino Acid

<400> SEQUENCE: 28

Leu Ile Ile Ala Leu Ser Val Xaa His Arg Gln Pro Ser Thr Met Ser
 1               5                  10                  15

Ser Thr Gly Gly Gly Asp Asp Gly Ala Lys Lys Ser Trp Pro Glu Val
            20                  25                  30

Val Gly Leu Ser Leu Glu Glu Ala Lys Arg Val Ile Leu Cys Asp Lys
            35                  40                  45

Pro Asp Ala Asp Ile Val Val Leu Pro Val Gly Thr Pro Val Thr Met
 50                  55                  60

Asp Phe Arg Pro Asn Arg Val Arg Ile Phe Val Asp Thr Val Ala Glu
 65                  70                  75                  80

Ala Xaa His Ile Gly
                85

<210> SEQ ID NO 29
<211> LENGTH: 382
<212> TYPE: DNA
<213> ORGANISM: Zea mays
<220> FEATURE:
<221> NAME/KEY: CDS
<222> LOCATION: (1)...(213)
<220> FEATURE:
<221> NAME/KEY: misc_feature
<222> LOCATION: (1)...(382)
<223> OTHER INFORMATION: n = A,T,C or G

<400> SEQUENCE: 29 gtg cgt cgt cgg cga aca gcc acc ggc ggc aag acg tcg tgg ccg gag        48
Val Arg Arg Arg Arg Thr Ala Thr Gly Gly Lys Thr Ser Trp Pro Glu
 1               5                  10                  15 gtg gtc ggg ctg agc gtc gag gaa gcc aag aag gtg att ctg gcg gac        96
Val Val Gly Leu Ser Val Glu Glu Ala Lys Lys Val Ile Leu Ala Asp
            20                  25                  30 aag ccg aac gcc gac atc gtg gtg ctg ccc acc acc acg cag gcg gtg       144
Lys Pro Asn Ala Asp Ile Val Val Leu Pro Thr Thr Thr Gln Ala Val
            35                  40                  45
```

```
acc tcc gac ttt ggg ttc gac cgt gtc cgc gtc ttc gtc ggg acc gtc      192
Thr Ser Asp Phe Gly Phe Asp Arg Val Arg Val Phe Val Gly Thr Val
    50                  55                  60 gcc cag acg ccc cat gtt ggc taggctagag cctcagccta gaggtcgtcg          243
Ala Gln Thr Pro His Val Gly
65                  70 gcaccgccgg ccatgaccac ctgctantat gtcactnact agtaataaag tatwaataac     303
agggaggatg catgctcatc nttggaatct gtacgcttgt tggactacta cttggctact     363
tgaaaaaaaa aaaaaaaaa                                                  382

<210> SEQ ID NO 30
<211> LENGTH: 71
<212> TYPE: PRT
<213> ORGANISM: Zea mays

<400> SEQUENCE: 30

Val Arg Arg Arg Thr Ala Thr Gly Gly Lys Thr Ser Trp Pro Glu
1               5                   10                  15

Val Val Gly Leu Ser Val Glu Glu Ala Lys Lys Val Ile Leu Ala Asp
                20                  25                  30

Lys Pro Asn Ala Asp Ile Val Val Leu Pro Thr Thr Thr Gln Ala Val
                35                  40                  45

Thr Ser Asp Phe Gly Phe Asp Arg Val Arg Val Phe Val Gly Thr Val
    50                  55                  60

Ala Gln Thr Pro His Val Gly
65                  70

<210> SEQ ID NO 31
<211> LENGTH: 448
<212> TYPE: DNA
<213> ORGANISM: Zea mays
<220> FEATURE:
<221> NAME/KEY: CDS
<222> LOCATION: (1)...(240)
<220> FEATURE:
<221> NAME/KEY: misc_feature
<222> LOCATION: (1)...(448)
<223> OTHER INFORMATION: n = A,T,C or G

<400> SEQUENCE: 31 cga ttt agc tat agc agg tct cga tcg gcg gcc atg agc ggt agc cgc      48
Arg Phe Ser Tyr Ser Arg Ser Arg Ser Ala Ala Met Ser Gly Ser Arg
1               5                   10                  15 agc aag aag tcg tgg ccg gag gtg gag ggg ctg ccg tcc gag gtg gcc      96
Ser Lys Lys Ser Trp Pro Glu Val Glu Gly Leu Pro Ser Glu Val Ala
                20                  25                  30 aag cag aaa att ctg gcc gac cgc ccg gac gtc cag gtg gtc gtt ctg      144
Lys Gln Lys Ile Leu Ala Asp Arg Pro Asp Val Gln Val Val Leu
            35                  40                  45 ccc gac ggc tcc ttc gtc acc act gat ttc aac gac aag cgc gtc cgg      192
Pro Asp Gly Ser Phe Val Thr Thr Asp Phe Asn Asp Lys Arg Val Arg
    50                  55                  60 gtc ttc gtc gac aac gcc gac aac gtc gcc aaa gtc ccc aag atc ggc      240
Val Phe Val Asp Asn Ala Asp Asn Val Ala Lys Val Pro Lys Ile Gly
65                  70                  75                  80 tagctagcta gctaggccca atcgttctaa tcagctagtt tctttctttc ataaataaaa     300
gtcctctctc gtacccggac tgtgatgttt ccctagttgt ctcgtacgtg ttgttttctg     360
tcttaatgga tgccatggcg cccgcgcgcg cctycatcat gaaaagctac atttgaaacg     420
attttnagta ttctttgctg ttaaaaaa                                        448
```

<210> SEQ ID NO 32
<211> LENGTH: 80
<212> TYPE: PRT
<213> ORGANISM: Zea mays

<400> SEQUENCE: 32

Arg Phe Ser Tyr Ser Arg Ser Arg Ser Ala Ala Met Ser Gly Ser Arg
1               5                   10                  15

Ser Lys Lys Ser Trp Pro Glu Val Glu Gly Leu Pro Ser Glu Val Ala
            20                  25                  30

Lys Gln Lys Ile Leu Ala Asp Arg Pro Asp Val Gln Val Val Val Leu
        35                  40                  45

Pro Asp Gly Ser Phe Val Thr Thr Asp Phe Asn Asp Lys Arg Val Arg
    50                  55                  60

Val Phe Val Asp Asn Ala Asp Asn Val Ala Lys Val Pro Lys Ile Gly
65                  70                  75                  80

<210> SEQ ID NO 33
<211> LENGTH: 67
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: (1)...(67)
<223> OTHER INFORMATION: Xaa = Any Essential Amino Acid
<220> FEATURE:
<221> NAME/KEY: VARIANT
<222> LOCATION: (1)...(67)
<223> OTHER INFORMATION: Xaa = Any Amino Acid

<400> SEQUENCE: 33

Xaa Xaa Xaa Xaa Lys Xaa Xaa Trp Pro Glu Leu Val Gly Lys Xaa Val
1               5                   10                  15

Glu Xaa Ala Asp Asp Xaa Ile Xaa Xaa Asp Lys Pro Glu Ala Xaa Ile
            20                  25                  30

Xaa Val Leu Pro Val Gly Thr Xaa Val Xaa Xaa Xaa Xaa Xaa Xaa Asp
        35                  40                  45

Xaa Val Xaa Leu Xaa Val Asp Lys Xaa Asp Xaa Xaa Ala Xaa Xaa Pro
    50                  55                  60

Xaa Xaa Gly
65

<210> SEQ ID NO 34
<211> LENGTH: 67
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: (1)...(67)
<223> OTHER INFORMATION: Xaa = Any Essential Amino Acid
<220> FEATURE:
<221> NAME/KEY: VARIANT
<222> LOCATION: (1)...(67)
<223> OTHER INFORMATION: Xaa = Any Amino Acid

<400> SEQUENCE: 34

Xaa Xaa Xaa Xaa Lys Xaa Xaa Trp Pro Glu Leu Val Gly Lys Xaa Xaa
1               5                   10                  15

Glu Xaa Ala Lys Lys Xaa Ile Xaa Xaa Asp Lys Pro Xaa Ala Xaa Ile

```
                   20                  25                  30
Xaa Val Leu Pro Xaa Gly Thr Xaa Val Xaa Xaa Xaa Xaa Xaa Xaa
            35                  40                  45

Xaa Val Xaa Leu Xaa Xaa Asp Lys Xaa Asp Xaa Xaa Ala Xaa Xaa Pro
        50                  55                  60

Xaa Xaa Gly
65

<210> SEQ ID NO 35
<211> LENGTH: 65
<212> TYPE: PRT
<213> ORGANISM: Hordeum vulgare

<400> SEQUENCE: 35

Gly Ala Lys Thr Ser Trp Pro Glu Val Val Gly Met Ser Ala Glu Lys
1               5                   10                  15

Ala Lys Glu Ile Ile Leu Arg Asp Lys Pro Asn Ala Gln Ile Glu Val
            20                  25                  30

Ile Pro Val Asp Ala Met Val Pro Leu Asn Phe Asn Pro Asn Arg Val
        35                  40                  45

Phe Val Leu Val His Lys Ala Thr Thr Val Ala Glx Val Ser Arg Val
    50                  55                  60

Gly
65

<210> SEQ ID NO 36
<211> LENGTH: 62
<212> TYPE: PRT
<213> ORGANISM: Hordeum vulgare

<400> SEQUENCE: 36

Gly Ala Lys Thr Glu Trp Pro Glu Leu Val Gly Cys Thr Ile Lys Glu
1               5                   10                  15

Ala Lys Glu Lys Ile Lys Ala Asp Arg Pro Asp Leu Lys Val Val Ile
            20                  25                  30

Val Pro Val Gly Ser Ile Val Thr Gln Glu Ile Asp Leu Asn Arg Val
        35                  40                  45

Arg Val Trp Val Asp Lys Val Ala Lys Val Pro Lys Ile Gly
    50                  55                  60

<210> SEQ ID NO 37
<211> LENGTH: 62
<212> TYPE: PRT
<213> ORGANISM: Zea mays

<400> SEQUENCE: 37

Gly Ala Lys Thr Ser Trp Pro Glu Val Val Gly Leu Ser Val Glu Asp
1               5                   10                  15

Ala Lys Lys Val Ile Leu Lys Asp Lys Pro Asp Ala Asp Ile Val Val
            20                  25                  30

Leu Pro Val Gly Ser Val Thr Ala Asp Tyr Arg Pro Asn Arg Val
        35                  40                  45

Arg Ile Phe Val Asp Ile Val Ala Gln Thr Pro His Ile Gly
    50                  55                  60

<210> SEQ ID NO 38
<211> LENGTH: 62
<212> TYPE: PRT
<213> ORGANISM: Vicia faba
```

-continued

<400> SEQUENCE: 38

Arg Thr Ser Trp Pro Glu Leu Val Gly Val Ser Ala Glu Glu Ala Arg
1               5                   10                  15

Lys Ile Lys Glu Glu Met Pro Glu Ala Glu Ile Gln Val Val Pro Gln
            20                  25                  30

Asp Ser Phe Val Thr Ala Asp Tyr Lys Phe Gln Arg Val Arg Leu Tyr
        35                  40                  45

Val Asp Glu Ser Asn Lys Val Val Arg Ala Ala Pro Ile Gly
50                  55                  60

<210> SEQ ID NO 39
<211> LENGTH: 66
<212> TYPE: PRT
<213> ORGANISM: Cucurbita maxima

<400> SEQUENCE: 39

Ala Glu Lys Ser Ser Trp Pro Glu Leu Val Gly Glu Asp Gly Glu Glu
1               5                   10                  15

Ala Val Lys Ile Ile Gln Gln Glu Asn Pro Ser Leu Asp Val Ile Leu
            20                  25                  30

Met Pro Arg Gly Gln Asn Trp Ala Thr Leu Asp Cys Arg Pro Asn Arg
        35                  40                  45

Val Arg Val Phe Asn Asp Glu Ser Gly Lys Val Asn Ser Ile Pro Arg
50                  55                  60

Ile Gly
65

<210> SEQ ID NO 40
<211> LENGTH: 64
<212> TYPE: PRT
<213> ORGANISM: Canavalia lineata

<400> SEQUENCE: 40

Thr Arg Lys Thr Ser Trp Pro Glu Leu Val Gly Val Thr Ala Glu Glu
1               5                   10                  15

Ala Glu Lys Ile Lys Glu Glu Met Ser Gly Val Glu Ile Gln Val Val
            20                  25                  30

Pro Pro Gly Ser Phe Val Thr Ala Asp Tyr Lys Pro Gln Arg Val Arg
        35                  40                  45

Leu Tyr Val Asp Glu Ser Asn Lys Val Thr Arg Thr Pro Gly Ile Gly
50                  55                  60

<210> SEQ ID NO 41
<211> LENGTH: 65
<212> TYPE: PRT
<213> ORGANISM: Vigna angularis

<400> SEQUENCE: 41

Pro Thr Lys Thr Ser Trp Pro Glu Leu Val Gly Val Thr Ala Glu Gln
1               5                   10                  15

Ala Glu Thr Lys Ile Lys Glu Glu Met Val Asp Val Gln Ile Gln Val
            20                  25                  30

Ser Pro His Asp Ser Phe Val Thr Ala Asp Tyr Asn Pro Lys Arg Val
        35                  40                  45

Arg Lys Tyr Val Asp Glu Ser Asn Lys Val Thr Arg Thr Pro Ser Ile
50                  55                  60

Gly

<210> SEQ ID NO 42
<211> LENGTH: 66
<212> TYPE: PRT
<213> ORGANISM: Nicotiana tabacum

<400> SEQUENCE: 42

Val Thr Lys Glu Arg Trp Pro Glu Leu Leu Gly Thr Pro Ala Lys Phe
1               5                   10                  15

Ala Met Gln Ile Ile Gln Lys Glu Asn Pro Lys Leu Thr Asn Val Gln
            20                  25                  30

Thr Val Leu Asn Gly Thr Pro Val Thr Glu Asp Leu Arg Cys Asn Arg
        35                  40                  45

Val Arg Leu Phe Val Asn Val Leu Asp Phe Val Val Gln Thr Pro Gln
    50                  55                  60

Val Gly
65

<210> SEQ ID NO 43
<211> LENGTH: 66
<212> TYPE: PRT
<213> ORGANISM: Nicotiana sylvestris

<400> SEQUENCE: 43

Asn Lys Lys Glu Thr Trp Pro Glu Leu Ile Gly Val Pro Ala Lys Phe
1               5                   10                  15

Ala Arg Glu Ile Ile Gln Lys Glu Asn Ser Lys Leu Thr Asn Val Pro
            20                  25                  30

Ser Val Leu Asn Gly Ser Pro Val Thr Lys Asp Phe Arg Cys Glu Arg
        35                  40                  45

Val Arg Leu Phe Val Asn Val Leu Asp Phe Val Val Gln Ile Pro Arg
    50                  55                  60

Val Gly
65

<210> SEQ ID NO 44
<211> LENGTH: 65
<212> TYPE: PRT
<213> ORGANISM: Sambucus nigra

<400> SEQUENCE: 44

Val Gly Lys Asn Thr Trp Pro Glu Leu Cys Gly Ala Arg Gly Glu Glu
1               5                   10                  15

Ala Ala Ala Thr Val Glu Thr Glu Asn Pro Ser Val Thr Ala Val Ile
            20                  25                  30

Val Pro Glu Gly Ser Ile Val Thr Thr Asp Glu Arg Cys Asp Arg Val
        35                  40                  45

Arg Val Trp Val Asp Glu Asn Gly Ile Val Thr Arg Val Pro Val Ile
    50                  55                  60

Gly
65

<210> SEQ ID NO 45
<211> LENGTH: 65
<212> TYPE: PRT
<213> ORGANISM: Momordica charantia

<400> SEQUENCE: 45

-continued

Gln Gly Lys Ser Ser Trp Pro Gln Leu Val Gly Ser Thr Gly Ala Ala
1               5                   10                  15

Ala Lys Ala Val Ile Glu Arg Glu Asn Pro Arg Val Arg Ala Val Ile
            20                  25                  30

Ile Lys Val Gly Ser Gly Ala Thr Lys Asp Phe Arg Cys Asp Arg Val
            35                  40                  45

Arg Val Trp Val Thr Glu Arg Gly Ile Val Ala Arg Pro Pro Thr Ile
    50                  55                  60

Gly
65

<210> SEQ ID NO 46
<211> LENGTH: 65
<212> TYPE: PRT
<213> ORGANISM: Cucurbita maxima

<400> SEQUENCE: 46

Pro Gly Lys Ser Ser Trp Pro His Leu Val Gly Val Gly Gly Ser Val
1               5                   10                  15

Ala Lys Ala Ile Ile Glu Arg Gln Asn Pro Asn Val Lys Ala Val Ile
            20                  25                  30

Leu Glu Glu Gly Thr Pro Val Thr Lys Asp Phe Arg Cys Asn Arg Val
            35                  40                  45

Arg Ile Trp Val Asn Lys Arg Gly Leu Val Val Ser Pro Pro Arg Ile
    50                  55                  60

Gly
65

<210> SEQ ID NO 47
<211> LENGTH: 66
<212> TYPE: PRT
<213> ORGANISM: Solanum tuberosum

<400> SEQUENCE: 47

Asp Gly Lys Leu Gln Trp Pro Glu Leu Ile Gly Val Pro Thr Lys Leu
1               5                   10                  15

Ala Lys Glu Ile Ile Glu Lys Gln Asn Ser Leu Ile Ser Asn Val His
            20                  25                  30

Ile Leu Leu Asn Gly Ser Pro Val Thr Met Asp Phe Arg Cys Asn Arg
            35                  40                  45

Val Arg Leu Phe Asp Asp Ile Leu Gly Ser Val Val Gln Ile Pro Arg
    50                  55                  60

Val Ala
65

<210> SEQ ID NO 48
<211> LENGTH: 66
<212> TYPE: PRT
<213> ORGANISM: Solanum tuberosum

<400> SEQUENCE: 48

Asn Gly Lys Leu Ser Trp Pro Glu Leu Ile Gly Val Pro Ala His Tyr
1               5                   10                  15

Ala Lys Gly Ile Ile Glu Lys Glu Asn Ser Leu Ile Thr Asn Val Gln
            20                  25                  30

Ile Leu Leu Asn Gly Ser Pro Val Thr Met Asp Tyr Arg Cys Asn Arg
            35                  40                  45

Val Arg Leu Phe Asp Asn Ile Leu Gly Asp Val Val Gln Ile Pro Arg

```
                       50                  55                  60
Val Ala
 65

<210> SEQ ID NO 49
<211> LENGTH: 66
<212> TYPE: PRT
<213> ORGANISM: Lycopersicon peruvianum

<400> SEQUENCE: 49

Lys Gly Lys Gln Phe Trp Pro Glu Leu Ile Gly Val Pro Ala Leu Tyr
 1               5                  10                  15

Ala Lys Gly Ile Ile Glu Lys Glu Asn Pro Ser Ile Thr Asn Ile Pro
                20                  25                  30

Ile Leu Leu Asn Gly Ser Pro Val Thr Lys Asp Phe Arg Cys Asp Arg
             35                  40                  45

Val Arg Leu Phe Val Asn Ile Leu Gly Asp Val Val Gln Ile Pro Arg
         50                  55                  60

Val Thr
 65

<210> SEQ ID NO 50
<211> LENGTH: 66
<212> TYPE: PRT
<213> ORGANISM: Lycopersicon esculentum

<400> SEQUENCE: 50

Val Thr Lys Glu Ser Trp Pro Glu Leu Leu Gly Thr Pro Ala Lys Phe
 1               5                  10                  15

Ala Lys Gln Ile Ile Gln Lys Glu Asn Pro Lys Leu Thr Asn Val Glu
                20                  25                  30

Thr Leu Leu Asn Gly Ser Ala Phe Thr Glu Asp Leu Arg Cys Asn Arg
             35                  40                  45

Val Arg Leu Phe Val Asn Leu Leu Asp Ile Val Val Gln Thr Pro Lys
         50                  55                  60

Val Gly
 65

<210> SEQ ID NO 51
<211> LENGTH: 66
<212> TYPE: PRT
<213> ORGANISM: Lycopersicon esculentum

<400> SEQUENCE: 51

Glu Gly Lys Gln Met Trp Pro Glu Leu Ile Gly Val Pro Thr Lys Leu
 1               5                  10                  15

Ala Lys Glu Ile Ile Glu Lys Glu Asn Pro Ser Ile Thr Asn Ile Pro
                20                  25                  30

Ile Leu Leu Ser Gly Ser Pro Ile Thr Leu Asp Tyr Leu Cys Asp Arg
             35                  40                  45

Val Arg Leu Phe Asp Asn Ile Leu Gly Phe Val Val Gln Met Pro Val
         50                  55                  60

Val Thr
 65

<210> SEQ ID NO 52
<211> LENGTH: 65
<212> TYPE: PRT
<213> ORGANISM: Amaranthus caudatus
```

-continued

```
<400> SEQUENCE: 52

Pro Gly Lys Gln Glu Trp Pro Glu Leu Val Gly Glu Tyr Gly Tyr Lys
1               5                   10                  15

Ala Ala Ala Ile Ile Glu Arg Glu Asn Pro Asn Val Arg Ser Ile Val
            20                  25                  30

Lys His Glu Arg Ser Gly Phe Thr Lys Asp Phe Arg Cys Asp Arg Val
        35                  40                  45

Trp Val Val Asp Ser Thr Gly Val Val Arg Thr Pro Arg Val
    50                  55                  60

Thr
65

<210> SEQ ID NO 53
<211> LENGTH: 65
<212> TYPE: PRT
<213> ORGANISM: Arabidopsis thaliana

<400> SEQUENCE: 53

Val Ile Phe Asn Ser Trp Ser Val Leu Thr Gly Thr Asn Gly Asp Tyr
1               5                   10                  15

Ala Ala Val Val Ile Glu Arg Glu Asn Pro Thr Val Asn Ala Ala Val
            20                  25                  30

Ile Leu Asp Gly Ser Pro Val Thr Ala Asp Phe Arg Cys Asp Arg Val
        35                  40                  45

Arg Val Phe Val Asp Gly Asn Arg Ile Val Val Lys Thr Pro Lys Ser
    50                  55                  60

Gly
65

<210> SEQ ID NO 54
<211> LENGTH: 104
<212> TYPE: DNA
<213> ORGANISM: Artificial Sequence
<220> FEATURE:
<223> OTHER INFORMATION: oligonucleotide

<400> SEQUENCE: 54
catgaagctg aagacagagt ggccggagtt ggtggggaaa tcggtggaga aagccaagaa      60
ggtgatcctg aaggacaagc cagaggcgca aatcatagtt ctgc                      104

<210> SEQ ID NO 55
<211> LENGTH: 106
<212> TYPE: DNA
<213> ORGANISM: Artificial Sequence
<220> FEATURE:
<223> OTHER INFORMATION: oligonucleotide

<400> SEQUENCE: 55
caaccggcag aactatgatt tgcgcctctg gcttgtcctt caggatcacc ttcttggctt      60
tctccaccga tttccccacc aactccggcc actctgtctt cagctt                    106

<210> SEQ ID NO 56
<211> LENGTH: 94
<212> TYPE: DNA
<213> ORGANISM: Artificial Sequence
<220> FEATURE:
<223> OTHER INFORMATION: oligonucleotide

<400> SEQUENCE: 56
```

```
cggttggtac aaaggtgacg aaggaatata agatcgaccg cgtcaagctc tttgtggata    60
aaaaggacaa catcgcgcag gtccccaggg tcgg                               94
```

<210> SEQ ID NO 57
<211> LENGTH: 92
<212> TYPE: DNA
<213> ORGANISM: Artificial Sequence
<220> FEATURE:
<223> OTHER INFORMATION: oligonucleotide

<400> SEQUENCE: 57

```
ctagccgacc ctggggacct gcgcgatgtt gtccttttta tccacaaaga gcttgacgcg    60
gtcgatctta tattccttcg tcacctttgt ac                                 92
```

<210> SEQ ID NO 58
<211> LENGTH: 26
<212> TYPE: DNA
<213> ORGANISM: Artificial Sequence
<220> FEATURE:
<223> OTHER INFORMATION: oligonucleotide

<400> SEQUENCE: 58

```
gtactagtca tgaagctgaa gacaga                                        26
```

<210> SEQ ID NO 59
<211> LENGTH: 28
<212> TYPE: DNA
<213> ORGANISM: Artificial Sequence
<220> FEATURE:
<223> OTHER INFORMATION: oligonucleotide

<400> SEQUENCE: 59

```
gagaagcttg ctagccgacc ctggggac                                      28
```

<210> SEQ ID NO 60
<211> LENGTH: 23
<212> TYPE: DNA
<213> ORGANISM: Artificial Sequence
<220> FEATURE:
<223> OTHER INFORMATION: oligonucleotide

<400> SEQUENCE: 60

```
ttttttcat gaagctgaag aca                                            23
```

<210> SEQ ID NO 61
<211> LENGTH: 30
<212> TYPE: DNA
<213> ORGANISM: Artificial Sequence
<220> FEATURE:
<223> OTHER INFORMATION: oligonucleotide

<400> SEQUENCE: 61

```
tttttttctcg aggctagccg accctgggga                                   30
```

<210> SEQ ID NO 62
<211> LENGTH: 35
<212> TYPE: DNA
<213> ORGANISM: Artificial Sequence
<220> FEATURE:
<223> OTHER INFORMATION: oligonucleotide

<400> SEQUENCE: 62

```
atcgacaagg tcaagctttt tgtggataaa aagga                              35
```

```
<210> SEQ ID NO 63
<211> LENGTH: 36
<212> TYPE: DNA
<213> ORGANISM: Artificial Sequence
<220> FEATURE:
<223> OTHER INFORMATION: oligonucleotide

<400> SEQUENCE: 63
cacctttgta ccaaccggta gaactatgat ttgcgc                           36

<210> SEQ ID NO 64
<211> LENGTH: 45
<212> TYPE: DNA
<213> ORGANISM: Artificial Sequence
<220> FEATURE:
<223> OTHER INFORMATION: oligonucleotide

<400> SEQUENCE: 64
gttggtacaa aggtggcgaa ggcctataag atcgacaagg tcaag                 45

<210> SEQ ID NO 65
<211> LENGTH: 39
<212> TYPE: DNA
<213> ORGANISM: Artificial Sequence
<220> FEATURE:
<223> OTHER INFORMATION: oligonucleotide

<400> SEQUENCE: 65 tttttctcg aggctagccg accctgggga cctgcgcta                         39

<210> SEQ ID NO 66
<211> LENGTH: 46
<212> TYPE: DNA
<213> ORGANISM: Artificial Sequence
<220> FEATURE:
<223> OTHER INFORMATION: oligonucleotide

<400> SEQUENCE: 66
ccggttggta caaaggtggg taagcattat aagatcgaca aggtca                46

<210> SEQ ID NO 67
<211> LENGTH: 46
<212> TYPE: DNA
<213> ORGANISM: Artificial Sequence
<220> FEATURE:
<223> OTHER INFORMATION: oligonucleotide

<400> SEQUENCE: 67
agcttgacct tgtcgatctt ataatgctta cccacctttg taccaa                46

<210> SEQ ID NO 68
<211> LENGTH: 82
<212> TYPE: DNA
<213> ORGANISM: Artificial Sequence
<220> FEATURE:
<223> OTHER INFORMATION: oligonucleotide

<400> SEQUENCE: 68 ttttttcat gaagtcggtg gagaagaaac cgaagggtgt gaagacaggt gcgggtgaca   60
agcataagct gaagacagag tg                                          82

<210> SEQ ID NO 69
<211> LENGTH: 46
<212> TYPE: DNA
<213> ORGANISM: Artificial Sequence
<220> FEATURE:
```

```
<223> OTHER INFORMATION: oligonucleotide

<400> SEQUENCE: 69
ccggttggta caaaggtgac gggcgaatac aagatcgacc gcgtca            46

<210> SEQ ID NO 70
<211> LENGTH: 46
<212> TYPE: DNA
<213> ORGANISM: Artificial Sequence
<220> FEATURE:
<223> OTHER INFORMATION: oligonucleotide

<400> SEQUENCE: 70
agcttgacgc ggtcgatctt gtattcgccc gtcacctttg taccaa            46

<210> SEQ ID NO 71
<211> LENGTH: 36
<212> TYPE: DNA
<213> ORGANISM: Artificial Sequence
<220> FEATURE:
<223> OTHER INFORMATION: oligonucleotide

<400> SEQUENCE: 71
ccggtgaatg gaagatggat cgcgtccgcc tctggg                       36

<210> SEQ ID NO 72
<211> LENGTH: 36
<212> TYPE: DNA
<213> ORGANISM: Artificial Sequence
<220> FEATURE:
<223> OTHER INFORMATION: oligonucleotide

<400> SEQUENCE: 72
tcgacccaga ggcggacgcg atccatcttc cattca                       36

<210> SEQ ID NO 73
<211> LENGTH: 43
<212> TYPE: DNA
<213> ORGANISM: Artificial Sequence
<220> FEATURE:
<223> OTHER INFORMATION: oligonucleotide

<400> SEQUENCE: 73 tttttttccat ggctaagatg aagtgcacgt ggcctgagct ggt              43

<210> SEQ ID NO 74
<211> LENGTH: 44
<212> TYPE: DNA
<213> ORGANISM: Artificial Sequence
<220> FEATURE:
<223> OTHER INFORMATION: oligonucleotide

<400> SEQUENCE: 74
ttttttaagc ttggatccct agccgcactt cggagtcttg gcga              44
```

What is claimed is:

1. An expression cassette comprising an isolated nucleic acid chosen from the group consisting of:
   (a) a polynucleotide that encodes the polypeptide of SEQ ID NOs: 6, 8, 10, 14, 16, 18, or 20; and
   (b) a polynucleotide comprising the sequence set forth in SEQ ID NOs: 5, 7, 9, 13, 15, 17, or 19 operably linked to a promoter and one or more of: a ribosome binding site, an RNA processing signal, a transcription termination site, a transit sequence, a polynucleotide encoding a transit peptide, a polynucleotide encoding a signal peptide, or a polyadenylation signal.

* * * * *